(12) United States Patent
Zhang et al.

(10) Patent No.: US 12,371,438 B2
(45) Date of Patent: Jul. 29, 2025

(54) GINKGOLIDE B DERIVATIVE AND SALT THEREOF, PREPARATION METHOD THEREFOR AND USE THEREOF

(71) Applicant: HUILING JINXIN (SHANGHAI) PHARMACEUTICAL TECHNOLOGY CO., LTD, Shanghai (CN)

(72) Inventors: Qian Zhang, Shanghai (CN); Jian Tang, Shanghai (CN)

(73) Assignee: HUILING JINXIN (SHANGHAI) PHARMACEUTICAL TECHNOLOGY CO., LTD, Shanghai (CN)

( * ) Notice: Subject to any disclaimer, the term of this patent is extended or adjusted under 35 U.S.C. 154(b) by 867 days.

(21) Appl. No.: 17/605,808

(22) PCT Filed: Mar. 3, 2020

(86) PCT No.: PCT/CN2020/077521
§ 371 (c)(1),
(2) Date: Oct. 22, 2021

(87) PCT Pub. No.: WO2020/215895
PCT Pub. Date: Oct. 29, 2020

(65) Prior Publication Data
US 2022/0204524 A1    Jun. 30, 2022

(30) Foreign Application Priority Data
Apr. 24, 2019 (CN) .......................... 201910338234.X

(51) Int. Cl.
*C07D 493/22* (2006.01)
*A61P 7/02* (2006.01)

(52) U.S. Cl.
CPC .............. *C07D 493/22* (2013.01); *A61P 7/02* (2018.01)

(58) Field of Classification Search
CPC   C07D 493/22; C07D 233/64; C07D 295/027; A61P 7/02; A61P 9/10;
(Continued)

(56) References Cited

U.S. PATENT DOCUMENTS

| 6,143,725 | A | 11/2000 | Vasella et al. | |
|---|---|---|---|---|
| 2003/0225052 | A1* | 12/2003 | Stromgaard | C07D 493/22 514/249 |
| 2019/0077811 | A1 | 3/2019 | Li et al. | |

FOREIGN PATENT DOCUMENTS

| CN | 1139435 A | | 1/1997 |
|---|---|---|---|
| CN | 1472214 A | * | 2/2004 |

(Continued)

OTHER PUBLICATIONS

Gupta D, Bhatia D, Dave V, Sutariya V, Varghese Gupta S. Salts of Therapeutic Agents: Chemical, Physicochemical, and Biological Considerations. Molecules. Jul. 14, 2018;23(7):1719. doi: 10.3390/molecules23071719. PMID: 30011904; PMCID: PMC6100526. (Year: 2018).*

(Continued)

*Primary Examiner* — Joseph K McKane
*Assistant Examiner* — Anna Grace Kuckla
(74) *Attorney, Agent, or Firm* — Maschoff Brennan

(57) ABSTRACT

The present invention relates to the technical field of medicine, and to derivatives represented by formula 1 and formula 2 in which a carboxylic acid group is introduced into the structure of Ginkgolide B by means of a hydroxyl group at the 10-position and ester derivatives of carboxylic acid groups, and pharmaceutically acceptable organic or inorganic salts. Ginkgolide B is used as a parent body and is prepared by means of chemical structure modification so as to achieve the goals of improving solubility, increasing bioavailability and enhancing healing efficacy. The prepared compound and carboxylate salts thereof have significant platelet activating factor antagonism, an anticoagulant effect and an anti-acute cerebral ischemia effect, and can be used for preparing a drug for preventing and treating ischemic stroke, thrombosis, angina pectoris, cardiopulmonary infarction, as well as inflammation, asthma and other diseases related to a platelet activating factor.

Formula 1

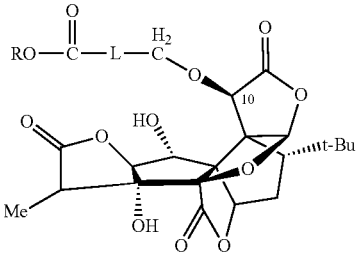

Formula 2

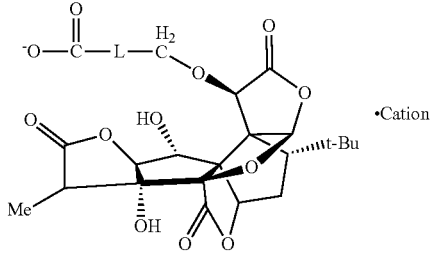

20 Claims, 3 Drawing Sheets

(58) Field of Classification Search
CPC .. A61P 9/04; A61P 11/00; A61P 11/06; A61P 29/00; C07C 211/05; C07C 211/07; C07C 215/10; C07C 257/14; C07C 229/26; Y02P 20/55

See application file for complete search history.

(56) References Cited

FOREIGN PATENT DOCUMENTS

| | | | | |
|---|---|---|---|---|
| CN | 1837212 | A | | 9/2006 |
| CN | 104098584 | A | * 10/2014 | ........... C07D 493/22 |
| CN | 109485674 | A | | 3/2019 |
| CN | 110054634 | A | | 7/2019 |
| JP | H01-151583 | A | | 6/1989 |
| JP | 2001-527568 | A | | 12/2001 |
| JP | 2019-506446 | A | | 3/2019 |
| WO | 2006083366 | A2 | | 8/2006 |

OTHER PUBLICATIONS

European Search Report issued in European Patent Application No. 20794825.8 Dated Jan. 11, 2023.
Lihong Hu et al. "Alkl and Alkoxycarbonyl Derivatives of Ginkgolide B: Synyhesis and Biological Evaluation of PAF Inhibitory Activity"Bioorganic and Medicinal Chemistry, vol. 8, p. 1515-21(2000).
Weiliang Zhu et al. "QSATR Analyses on Ginkogolides and their Analogues using CMFA, COMSIA and HQSAR" Bioorganic and Medicinal Chemistry, vol. 13, p. 313-22(2005).
JP Office Action dated Jan. 9, 2024 as received in Application No. 2021-563713.
International Search Report dated Apr. 26, 2020 issued in PCT application No. PCT/CN2020/077521.
Written Opinion of International Search Authority dated Apr. 26, 2020 issued in PCT application No. PCT/CN2020/077521.
"STN:Registry" 913942-98-0, Nov. 22, 2006 p. 2.

* cited by examiner

Figure 4

GINKGOLIDE B DERIVATIVE AND SALT THEREOF, PREPARATION METHOD THEREFOR AND USE THEREOF

The present application claims the priority of Chinese patent application CN201910338234.X filed on Apr. 24, 2019. This application refers to the full text of the above-mentioned Chinese patent application.

TECHNICAL FIELD

The present disclosure belongs to the technical field of medicine, and relates to Ginkgolide B carboxylic acid derivatives and esters thereof, and the corresponding salts of Ginkgolide B carboxylic acid derivatives, and specifically relates to Ginkgolide B carboxylic acid derivatives and esters thereof and preparation methods therefor and uses thereof. The present disclosure uses Ginkgolide B as a parent body, and the Ginkgolide B derivatives are prepared by chemical structure modification, so as to achieve the purposes of changing the solubility, improving the bioavailability and enhancing the curative effect.

BACKGROUND

It has been recorded that *Ginkgo biloba* was used in our folklore around 1000 AD to treat asthma and bronchitis. In recent times, with the standardization of drug extraction process and in-depth research on pharmacological action activity, *Ginkgo biloba* extract (GBE) has been widely used in the world, especially in Germany, France and other European countries for the treatment of diseases such as respiratory system and cardiovascular system.

The prior art discloses that Ginkgolide B (GB) is a diterpenoid compound extracted from *Ginkgo biloba*; biological activity evaluation shows that Ginkgolide B is the most active natural product of platelet activating factor (PAF) antagonist found to date. Platelet activating factor can promote the aggregation of platelets and neutrophils, and participate in various inflammatory reaction processes, thereby increasing vascular permeability, promoting thrombosis and inducing smooth muscle contraction, and playing an important role in the occurrence and development of a series of related diseases such as inflammation, asthma, cardiovascular and cerebrovascular microcirculation disturbance, gastrointestinal mucosal damage, etc. At the same time, studies have found that Ginkgolide B also has a strong anti-inflammatory effect. In the inflammatory reaction, the phospholipid of neutrophil membrane is hydrolyzed into arachidonic acid (AA) by LPA of activated phospholipase A2, and AA is further metabolized into products such as leukotrienes (LTs) and hydroxyeicosatetraenoic acid (HETEs) under the action of 5-lipoxygenase (5-LO), wherein some products are important inflammatory mediators, and the activation of phospholipase A2 requires the participation of intracellular calcium, ginkgolide B has an effect on arachidonic acid metabolic enzyme and intracellular free calcium in rat neutrophils, and its anti-inflammatory effect may be related to its inhibition of lysosomal enzyme release in neutrophils, production of superoxide anion and increase of intracellular calcium level.

At present, the varieties of Ginkgolide drugs in clinical use mainly include two categories of Ginkgolide mixed extracts including Ginkgolide B components and Ginkgolide B as the main component, which are mainly used for the treatment of thrombosis, acute pancreatitis and cardiovascular diseases, and the treatment of metastatic cancer, the protective effect on damaged neurons, etc. However, practice shows that Ginkgolide B has strong structural rigidity, poor water solubility and poor bioavailability due to its six-ring cage-like structural characteristics of diterpenoid compounds, which limits the full play of its efficacy and affects its clinical use effect.

Based on the current state of the prior art, the inventors of the present disclosure intend to provide Ginkgolide B carboxylic acid derivatives and esters thereof and preparation methods therefor and use thereof. The present disclosure uses Ginkgolide B as a parent body, and the Ginkgolide B derivative is prepared by chemical structure modification, so as to achieve the purposes of changing its water solubility, improving the bioavailability and enhancing the curative effect.

CONTENT OF THE PRESENT INVENTION

The purpose of the present disclosure is to provide a new class of Ginkgolide B carboxylic acid derivatives and esters thereof, and the Ginkgolide B carboxylic acid derivatives may be made into corresponding organic bases or inorganic base salts. The present disclosure obtains a new class of Ginkgolide B carboxylic acid derivatives and esters thereof through structural modification of Ginkgolide B by introducing various group containing carboxyl and ester groups thereof on hydroxyl at the 10-position, which may improve the solubility and overcome the unfavorable factors such as poor bioavailability of Ginkgolide B.

The present invention provides a compound represented by formula 1,

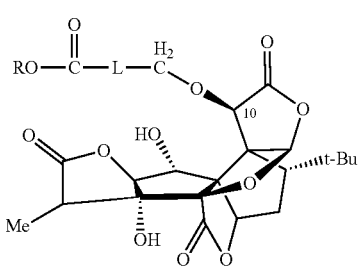

Formula 1 wherein,

L is heteroatom, substituted or unsubstituted $C_{1-10}$ hydrocarbonylene, substituted or unsubstituted $C_{1-10}$ heterohydrocarbonylene containing heteroatoms, or not existed; when L is heteroatom or substituted or unsubstituted $C_{1-10}$ heterohydrocarbonylene containing heteroatoms, the heteroatoms are selected from one or more of oxygen, nitrogen and sulfur; when there are multiple heteroatoms, the heteroatoms are the same or different;

R is hydrogen or substituted or unsubstituted $C_{1-8}$ hydrocarbonyl;

wherein the substituent in the substituted $C_{1-10}$ hydrocarbonylene, the substituted $C_{1-10}$ heterohydrocarbonylene containing heteroatoms and the substituted $C_{1-8}$ hydrocarbonyl is independently one or more of halogen, hydroxyl, $C_{1-10}$ alkoxy, phenyl and $C_{1-10}$ alkyl, and when multiple substituents exist, the substituents are the same or different;

The compound represented by formula 1 is not:

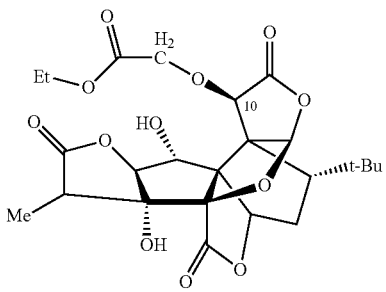

In a preferred embodiment of the present disclosure, when the substituent in the substituted $C_{1-10}$ hydrocarbonylene, the substituted $C_{1-10}$ heterohydrocarbonylene containing heteroatoms and the substituted $C_{1-8}$ hydrocarbonyl is halogen, the halogen is preferably fluorine, chlorine, bromine or iodine.

In a preferred embodiment of the present disclosure, when the substituent in the substituted $C_{1-10}$ hydrocarbonylene, the substituted $C_{1-10}$ heterohydrocarbonylene containing heteroatoms and the substituted $C_{1-8}$ hydrocarbonyl is $C_{1-10}$ alkoxy, the $C_{1-10}$ alkoxy is preferably $C_{1-4}$ alkoxy, more preferably methoxy, ethoxy, n-propoxy, isopropoxy, n-butoxy, isobutoxy or tert-butoxy.

In a preferred embodiment of the present disclosure, when the substituent in the substituted $C_{1-10}$ hydrocarbonylene, the substituted $C_{1-10}$ heterohydrocarbonylene containing heteroatoms and the substituted $C_{1-8}$ hydrocarbonyl is $C_{1-10}$ alkyl, the $C_{1-10}$ alkyl is preferably $C_{1-4}$ alkyl, more preferably methyl, ethyl, n-propyl, isopropyl, n-butyl, isobutyl or tert-butyl.

In the present disclosure, the term hydrocarbonylene refers to a group containing two types of atoms of carbon and hydrogen, and is the group remaining after the loss of any two hydrogen atoms from the corresponding hydrocarbon. The term hydrocarbonylene is preferably alkylene, alkenylene, alkynylene, cycloalkylene, cycloalkenylene, cycloalkynylene or arylene.

In the present disclosure, the term alkenylene refers to chain alkenylene, wherein the number of carbon-carbon double bonds is one or more, and the carbon-carbon double bonds may be located at any position of chain alkenylene.

In the present disclosure, the term alkynylene refers to chain alkynylene, wherein the number of carbon-carbon triple bonds is one or more, and the carbon-carbon triple bonds may be located at any position of chain alkynylene.

In the present disclosure, the term cycloalkenylene refers to cyclic alkenylene, wherein the number of carbon-carbon double bonds is one or more, and the carbon-carbon double bonds may be located at any position of cyclic alkenylene.

In the present disclosure, the term cycloalkynylene refers to cyclic alkynylene, wherein the number of carbon-carbon triple bonds is one or more, and the carbon-carbon triple bonds may be located at any position of cyclic alkynylene.

In the present disclosure, the term hydrocarbonyl refers to a group containing two types of atoms of carbon and hydrogen, and is the group remaining after the loss of any one hydrogen atom from the corresponding hydrocarbon. The term hydrocarbonyl is preferably alkyl, alkenyl, alkynyl, cycloalkyl, cycloalkenyl, cycloalkynyl or aryl.

In the present disclosure, the term alkenyl refers to chain alkenyl, wherein the number of carbon-carbon double bonds is one or more, and the carbon-carbon double bonds may be located at any position of chain alkenyl.

In the present disclosure, the term alkynyl refers to chain alkynyl, wherein the number of carbon-carbon triple bonds is one or more, and the carbon-carbon triple bonds may be located at any position of chain alkynyl.

In the present disclosure, the term cycloalkenyl refers to cyclic alkenyl, wherein the number of carbon-carbon double bonds is one or more, and the carbon-carbon double bonds may be located at any position of cyclic alkenyl.

In the present disclosure, the term cycloalkynyl refers to cyclic alkynyl, wherein the number of carbon-carbon triple bonds is one or more, and the carbon-carbon triple bonds may be located at any position of cyclic alkynyl.

In the present disclosure, the term heteroalkyl refers to the hydrocarbonylene of the present disclosure containing one or more heteroatoms inserted at any position. Wherein, the hydrocarbonylene is as defined above.

In the present disclosure, the term chain includes straight chain and branched chain.

In the present disclosure, the term cycloalkyl is preferably $C_3$-$C_{10}$ cycloalkyl, more preferably $C_3$-$C_6$ cycloalkyl. Examples of cycloalkyl include, but are not limited to: cyclopropyl, cyclobutyl, cyclopentyl and cyclohexyl.

In the present disclosure, the term aryl is preferably $C_6$-$C_{10}$ aryl. Examples of aryl include, but are not limited to: phenyl, naphthyl, or tetrahydronaphthyl.

In the present disclosure, the term heteroarylene is preferably $C_1$-$C_{10}$ heteroarylene containing 1, 2, 3 or 4 heteroatoms selected from O, N and S, further preferably $C_1$-$C_8$ heteroarylene containing 1, 2, 3 or 4 heteroatoms selected from O, N and S, and more preferably $C_1$-$C_6$ heteroarylene containing 1, 2, 3 or 4 heteroatoms selected from O, N and S.

In the present disclosure, the term alkyl includes branched and straight chain saturated aliphatic hydrocarbonyl, preferably containing 1-10 carbon atoms. Examples of alkyl include but are not limited to methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, and various isomers thereof.

In the present disclosure, the alkyl is preferably $C_1$-$C_4$ alkyl, more preferably methyl, ethyl, n-propyl, isopropyl, n-butyl, isobutyl or tert-butyl.

In a preferred embodiment of the present disclosure, the $C_{1-10}$ hydrocarbonylene in the "substituted or unsubstituted $C_{1-10}$ hydrocarbonylene" is preferably $C_{1-10}$ alkylene, $C_{2-10}$ alkenylene, $C_{2-10}$ alkynylene, $C_{3-10}$ cycloalkylene, $C_{3-10}$ cycloalkenylene, $C_{4-10}$ cycloalkynylene, phenylene or naphthylene.

In a preferred embodiment of the present disclosure, the $C_{1-10}$ hydrocarbonylene in the "substituted or unsubstituted $C_{1-10}$ hydrocarbonylene" is preferably $C_{3-10}$ alkylene, $C_{2-10}$ alkenylene, $C_{2-10}$ alkynylene, $C_{3-10}$ cycloalkylene, $C_{3-10}$ cycloalkenylene, $C_{4-10}$ cycloalkynylene, phenylene or naphthylene.

In a preferred embodiment of the present disclosure, the $C_{1-10}$ heterohydrocarbonylene in the "substituted or unsubstituted $C_{1-10}$ heterohydrocarbonylene containing heteroatoms" is preferably $C_{1-10}$ heteroalkylene, $C_{2-10}$ heteroalkenylene, $C_{2-10}$ heteroalkynylene, $C_{2-10}$ heterocycloalkylene, $C_{2-10}$ heterocycloalkenylene, $C_{2-10}$ heteroalkenylene or $C_{1-10}$ heteroarylene.

In a preferred embodiment of the present disclosure, the $C_{1-8}$ hydrocarbonyl in the "substituted or unsubstituted $C_{1-8}$ hydrocarbonyl" is preferably $C_{1-8}$ alkyl, $C_{2-8}$ alkenyl, $C_{2-8}$ alkynyl, $C_{3-8}$ cycloalkyl, $C_{3-8}$ cycloalkenyl, $C_{4-8}$ cycloalkenyl or phenyl.

In a preferred embodiment of the present disclosure, the L is preferably heteroatom, substituted or unsubstituted $C_{1-10}$ alkylene, substituted or unsubstituted $C_{2-10}$ alkenylene, substituted or unsubstituted $C_{2-10}$ alkynylene, substituted or unsubstituted $C_{3-10}$ cycloalkylene, substituted or unsubstituted $C_{3-10}$ cycloalkenylene, substituted or unsubstituted $C_{4-10}$ cycloalkynylene, substituted or unsubstituted phenylene, substituted or unsubstituted naphthylene, substituted or unsubstituted $C_{1-10}$ heteroalkylene, substituted or unsubstituted $C_{2-10}$ heteroalkenylene, substituted or unsubstituted $C_{2-10}$ heteroalkynylene, substituted or unsubstituted $C_{2-10}$ heterocycloalkylene, substituted or unsubstituted $C_{2-10}$ heterocycloalkenylene, substituted or unsubstituted $C_{2-10}$ heterocycloalkynylene, substituted or unsubstituted $C_{1-10}$ heteroarylene, or not existed.

In a preferred embodiment of the present disclosure, the R is preferably hydrogen, methyl, benzyl, substituted or unsubstituted $C_{3-8}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, or substituted or unsubstituted $C_{4-8}$ cycloalkynyl, or substituted or unsubstituted phenyl.

In a preferred embodiment of the present disclosure, when the L is a heteroatom, the heteroatom is preferably oxygen or sulfur.

In a preferred embodiment of the present disclosure, when the L is substituted or unsubstituted $C_{1-10}$ alkylene, the $C_{1-10}$ alkylene in the "substituted or unsubstituted $C_{1-10}$ alkylene" is preferably $C_{1-8}$ alkylene, further preferably methylene, ethylene, n-propylene, isopropylene, n-butylene, tert-butylene, or n-pentylene.

In a preferred embodiment of the present disclosure, when the L is substituted or unsubstituted $C_{2-10}$ alkenylene, the $C_{2-10}$ alkenylene in the "substituted or unsubstituted $C_{2-10}$ alkenylene" is preferably $C_{2-5}$ alkenylene, more preferably vinylene, propylene, butylene or pentenylene, further more preferably vinylene, and most preferably —CH═CH—.

In a preferred embodiment of the present disclosure, when the L is substituted or unsubstituted $C_{2-10}$ alkynylene, the $C_{2-10}$ alkynylene in the "substituted or unsubstituted $C_{2-10}$ alkynylene" is preferably $C_{2-5}$ alkynylene, and more preferably ethynylene, propynylene, butynylene or pentynylene.

In a preferred embodiment of the present disclosure, when the L is substituted or unsubstituted $C_{3-10}$ cycloalkylene, the $C_{3-10}$ cycloalkylene in the "substituted or unsubstituted $C_{3-10}$ cycloalkylene" is preferably $C_{3-8}$ cycloalkylene, further preferably cyclopropylene, cyclobutylene, cyclopentylene, cyclohexylene, cycloheptylene or cyclooctylene.

In a preferred embodiment of the present disclosure, when the L is substituted or unsubstituted $C_{3-10}$ cycloalkenylene, the $C_{3-10}$ cycloalkenylene in the "substituted or unsubstituted $C_{3-10}$ cycloalkenylene" is preferably $C_{3-8}$ cycloalkenylene, further preferably cyclopropenylene, cyclobutenylene, cyclopentenylene, cyclohexenylene, cycloheptenylene or cyclooctenylene.

In a preferred embodiment of the present disclosure, when the L is substituted or unsubstituted $C_{1-10}$ heteroalkylene containing heteroatoms, the $C_{1-10}$ heteroalkylene in the "substituted or unsubstituted $C_{1-10}$ heteroalkylene containing heteroatoms" is preferably $C_{1-6}$ heteroalkylene, further preferably $C_{1-4}$ heteroalkylene, further more preferably heteromethylene, heteroethylene, heteropropylene, heteroisopropylene, hetero-n-butylene, heteroisobutylene or hetero-tert-butyl, still further preferably heteroethylene or hetero-tert-butyl, wherein the heteroatom is preferably oxygen or sulfur, the number of heteroatoms is preferably 1 or 2, and the $C_{1-10}$ heteroalkylene is most preferably —CH$_2$OCH$_2$— or —CH$_2$OCH$_2$CH$_2$OCH$_2$—.

In a preferred embodiment of the present disclosure, when the L is substituted or unsubstituted $C_{2-10}$ heteroalkenylene, the $C_{2-10}$ heteroalkenylene in the "substituted or unsubstituted $C_{2-10}$ heteroalkenylene" is preferably $C_{2-5}$ heteroalkenylene, further preferably heterovinylene, heteropropenylene, heterobutenylene or heteropentenylene, wherein the heteroatom is preferably oxygen or sulfur, and the number of heteroatoms is preferably 1 or 2, and the $C_{2-10}$ heteroalkenylene is most preferably —CH═CH—O—CH$_2$—, —CH═CH—O—, —CH$_2$OCH═CHOCH$_2$— or —CH═CH—S—CH$_2$—.

In a preferred embodiment of the present disclosure, when the L is substituted or unsubstituted $C_{2-10}$ heteroalkynylene, the $C_{2-10}$ heteroalkynylene in the "substituted or unsubstituted $C_{2-10}$ heteroalkynylene" is preferably $C_{2-4}$ heteroalkynylene, further preferably heteroethynylene, heteropropynylene, heterobutynylene or heteropentynylene, wherein the heteroatom is preferably oxygen or sulfur, and the number of heteroatoms is preferably 1 or 2, and the $C_{2-10}$ heteroalkynylene is most preferably —C≡C—O—CH$_2$—, —C≡C—O—, —CH$_2$OC≡COCH$_2$— or —C≡C—S—CH$_2$—.

In a preferred embodiment of the present disclosure, when the L is substituted or unsubstituted $C_{2-10}$ heterocycloalkylene, the $C_{2-10}$ heterocycloalkylene in the "substituted or unsubstituted $C_{2-10}$ heterocycloalkylene" is preferably $C_{2-5}$ heterocycloalkylene, further more preferably heterocycloethylene, heterocyclopropylene, heterobutylene or heteropentylene, wherein the heteroatom is preferably oxygen or sulfur, and the number of heteroatoms is preferably 1 or 2.

In a preferred embodiment of the present disclosure, when the L is substituted or unsubstituted $C_{2-10}$ heterocycloalkenylene, the $C_{2-10}$ heterocycloalkenylene in the "substituted or unsubstituted $C_{2-10}$ heterocycloalkenylene" is preferably $C_{2-5}$ heterocycloalkenylene, further preferably heterocyclovinylene, heterocyclopropenylene, heterocyclobutenylene or heterocyclopentenylene, wherein, the heteroatom is preferably oxygen or sulfur, and the number of heteroatoms is preferably 1 or 2.

In a preferred embodiment of the present disclosure, when the L is substituted or unsubstituted $C_{1-10}$ heteroarylene, the $C_{1-10}$ heteroarylene in the "substituted or unsubstituted $C_{1-10}$ heteroarylene" is preferably $C_{1-9}$ heteroarylene, wherein the heteroatom is preferably oxygen or nitrogen, and the number of heteroatoms is preferably 1, 2, 3 or 4.

In a preferred embodiment of the present disclosure, when the R is substituted or unsubstituted $C_{1-8}$ alkyl, the $C_{1-8}$ alkyl in the "substituted or unsubstituted $C_{1-8}$ alkyl" is preferably n-propyl, isopropyl, n-butyl, isobutyl or tert-butyl.

In a preferred embodiment of the present disclosure, when the R is substituted or unsubstituted $C_{3-8}$ alkyl, the $C_{3-8}$ alkyl in the "substituted or unsubstituted $C_{3-8}$ alkyl" is preferably n-propyl, isopropyl, n-butyl, isobutyl or tert-butyl.

In a preferred embodiment of the present disclosure, when the R is substituted or unsubstituted $C_{2-8}$ alkenyl, the $C_{2-8}$ alkenyl in the "substituted or unsubstituted $C_{2-8}$ alkenyl" is preferably $C_{2-5}$ alkenyl, further preferably vinyl, propenyl, butenyl or pentenyl.

In a preferred embodiment of the present disclosure, when the R is substituted or unsubstituted $C_{2-8}$ alkynyl, the $C_{2-10}$ alkynyl in the "substituted or unsubstituted $C_{2-8}$ alkynyl" is preferably $C_{2-5}$ alkynyl, further preferably ethynyl, propynyl, butynyl or pentynyl.

In a preferred embodiment of the present disclosure, when the R is substituted or unsubstituted $C_{3-8}$ cycloalkyl, the $C_{3-8}$ cycloalkyl in the "substituted or unsubstituted $C_{3-8}$ cycloalkyl" is preferably cyclopropyl, cyclobutyl, cyclopentyl, cyclohexyl, cycloheptyl or cyclooctyl.

In a preferred embodiment of the present disclosure, when the R is substituted or unsubstituted $C_{3-8}$ cycloalkenyl, the $C_{3-8}$ cycloalkenyl in the "substituted or unsubstituted $C_{3-8}$ cycloalkenyl" is preferably cyclopropenyl, cyclobutenyl, cyclopentenyl, cyclohexenyl, cycloheptenyl or cyclooctenyl.

In a preferred embodiment of the present disclosure, the L is preferably substituted or unsubstituted $C_{2-10}$ alkenylene, substituted or unsubstituted $C_{1-10}$ heteroalkylene, or not existed.

In a preferred embodiment of the present disclosure, the R is preferably hydrogen, methyl, benzyl, or substituted or unsubstituted $C_{3-8}$ alkyl.

In a preferred embodiment of the present disclosure, the L is preferably —CH=CH—, —CH$_2$OCH$_2$—, —CH$_2$OCH$_2$CH$_2$OCH$_2$— or L is not existed.

In a preferred embodiment of the present disclosure, the R is preferably hydrogen, methyl or tert-butyl.

In a preferred embodiment of the present disclosure, the compound represented by formula 1 or the pharmaceutically acceptable salt thereof is selected from any of the following compounds:

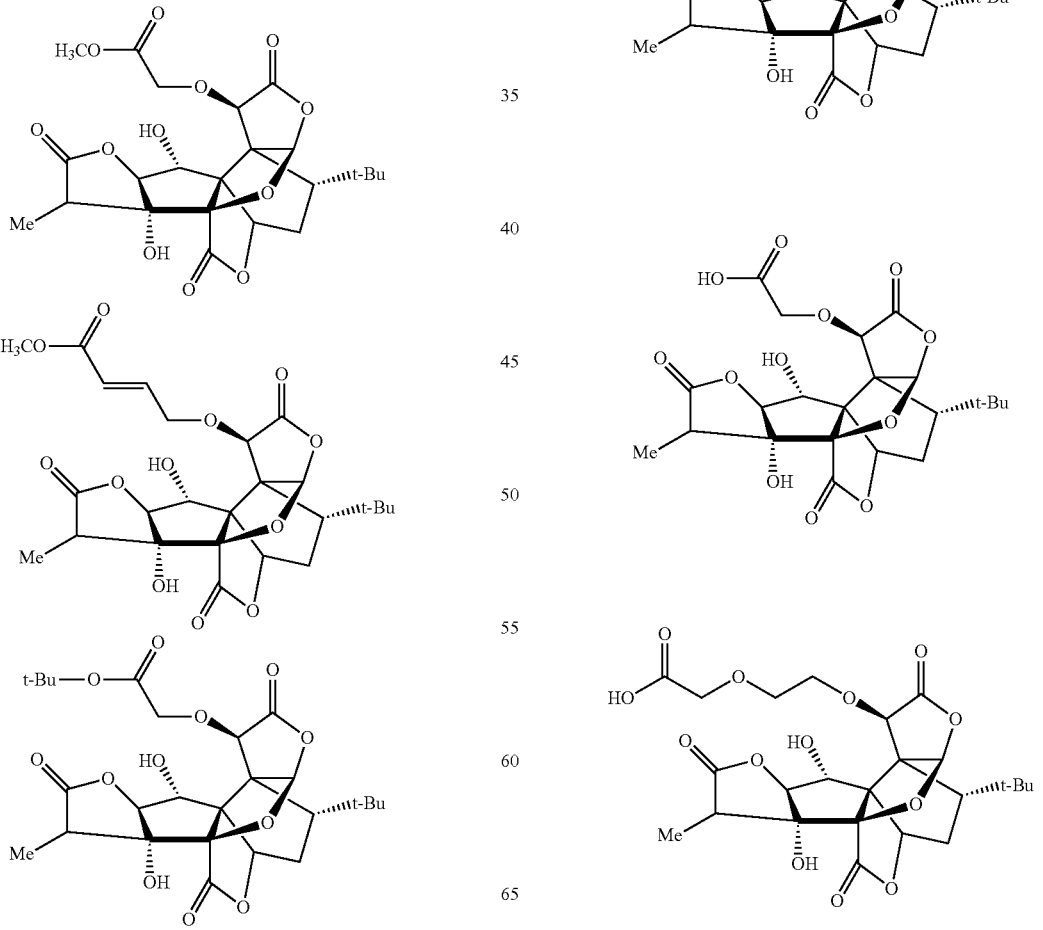

-continued

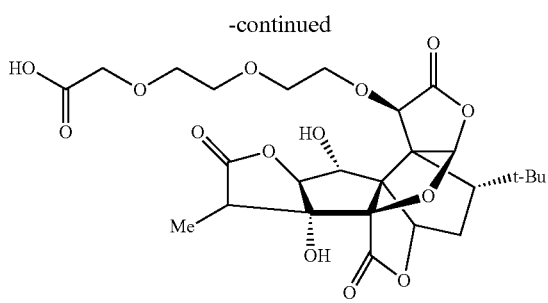

The present disclosure also provides a compound represented by formula 2:

Formula 2

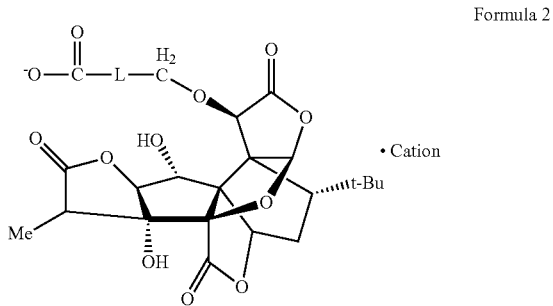

Wherein, L is as defined above;

cations, including cations formed from various inorganic and organic bases; the cations formed from inorganic bases may preferably be selected from sodium, potassium, calcium, magnesium, zinc, or ammonium cations etc., but are not limited to these salts; the cations formed from organic bases may preferably be selected from primary amines containing substituted or unsubstituted $C_{1-8}$ hydrocarbonyl, secondary amines containing substituted or unsubstituted $C_{1-8}$ hydrocarbonyl, nitrogen positive cations formed from tertiary amines containing substituted or unsubstituted $C_{1-8}$ hydrocarbonyl, and nitrogen positive cations formed from natural or non-natural amino acids, but are not limited to these salts.

In the present disclosure, the primary amine containing substituted or unsubstituted $C_{1-8}$ hydrocarbonyl refers to an amine formed by substituting a hydrogen atom on the ammonia with a substituted or unsubstituted $C_{1-8}$ hydrocarbonyl; wherein the substituted or unsubstituted $C_{1-8}$ hydrocarbonyl is as described above.

In the present disclosure, the secondary amine containing substituted or unsubstituted $C_{1-8}$ hydrocarbonyl refers to an amine formed by substituting two hydrogen atoms on the ammonia with two substituted or unsubstituted $C_{1-8}$ hydrocarbonyl, respectively, the two substituted or unsubstituted $C_{1-8}$ hydrocarbonyl may be the same or different, and the two substituted or unsubstituted $C_{1-8}$ hydrocarbonyl may form a ring in either manner (as long as it does not violate the common sense in the art), forming a ring such as pyrrolidine, piperidine, morpholine or thiomorpholine, etc.; wherein the substituted or unsubstituted $C_{1-8}$ hydrocarbonyl is as described above.

In the present disclosure, the tertiary amine containing substituted or unsubstituted $C_{1-8}$ hydrocarbonyl refers to an amine formed by substituting three hydrogen atoms on the ammonia with three substituted or unsubstituted $C_{1-8}$ hydrocarbonyl, the three substituted or unsubstituted $C_{1-8}$ hydrocarbonyl may be the same or different, and two or three substituted or unsubstituted $C_{1-8}$ hydrocarbonyl among the three substituted or unsubstituted $C_{1-8}$ hydrocarbonyl may form a ring in either manner (as long as it does not violate the common sense in the field); wherein, the substituted or unsubstituted $C_{1-8}$ hydrocarbonyl is as described above.

In the present disclosure, the natural or non-natural amino acids are those various types of amines containing carboxyl groups on their hydrocarbon chain, preferably L-arginine, L-histidine, L-lysine, D-arginine, D-histidine, D-lysine.

In a preferred embodiment of the present disclosure, the inorganic base in the cations formed by various inorganic bases and organic bases is preferably sodium carbonate, sodium bicarbonate, sodium hydroxide, potassium carbonate, calcium hydroxide, magnesium carbonate, magnesium hydroxide, ammonium hydroxide or zinc hydroxide.

In a preferred embodiment of the present disclosure, the organic base in the cations formed by various inorganic bases and organic bases may be amine compound, or natural or non-natural amino acid compound. The amine compounds are particularly preferably methylamine, dimethylamine, trimethylamine, ethylamine, diethylamine, triethylamine, propylamine, butylamine, pentylamine, hexylamine, N-methyl-D-glucosamine, pyrrolidine, morpholine and thiomorpholine. The amino acid compounds are preferably L-lysine, L-histidine, L-arginine, D-lysine, D-histidine and D-arginine.

In a preferred embodiment of the present disclosure, the cation in the compound represented by formula 2 is preferably

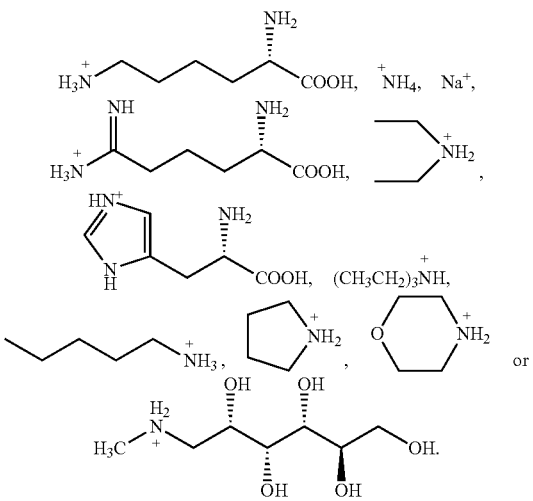

In a preferred embodiment of the present disclosure, the compound represented by formula 2 is selected from any of the following compounds:

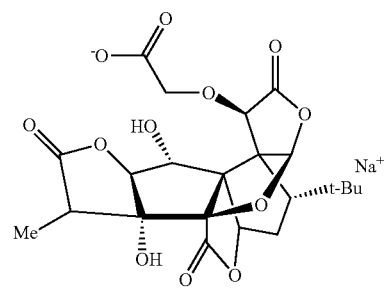

11
-continued

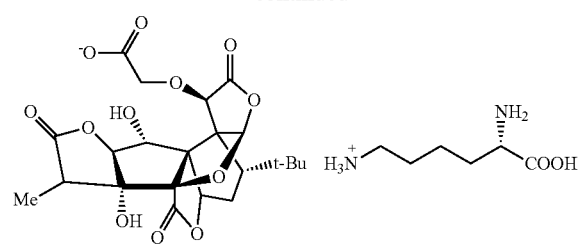

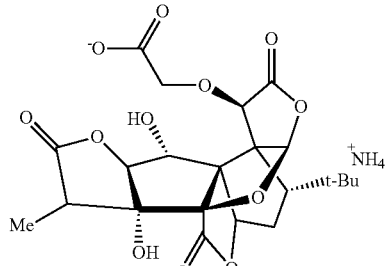

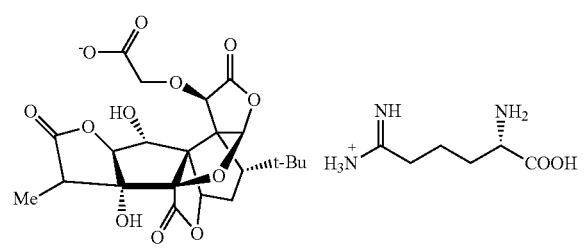

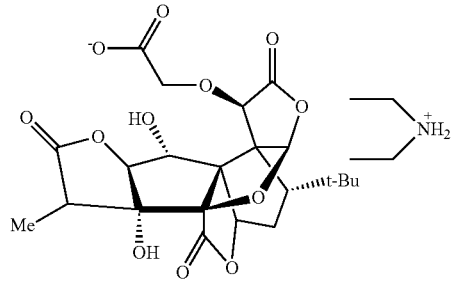

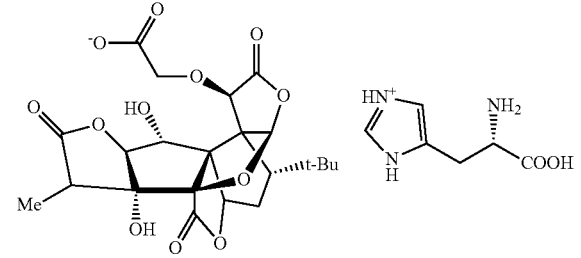

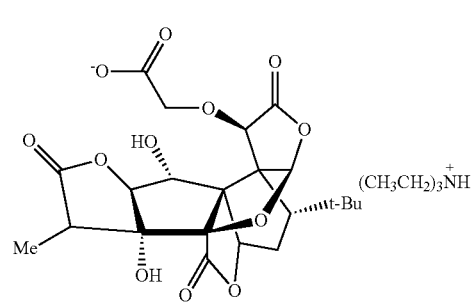

12
-continued

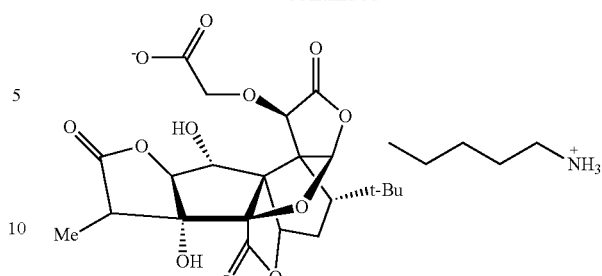

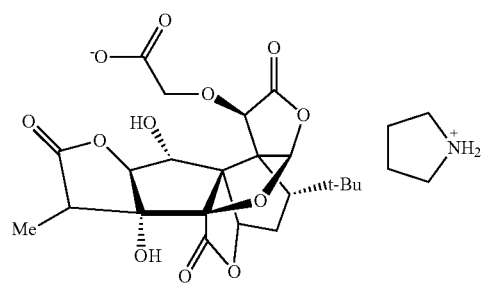

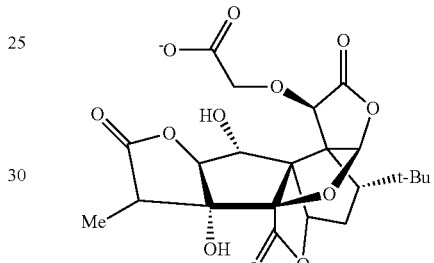

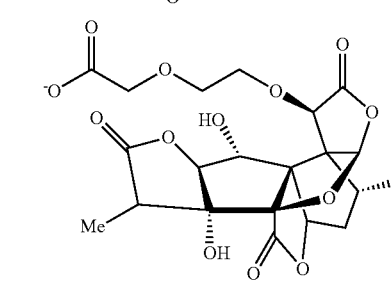

The present disclosure also provides a method for preparing a compound represented by formula 1 or a pharmaceutically acceptable salt thereof, comprising the following steps:

In an organic solvent, under the action of a base and a catalyst, Ginkgolide B and the compound represented by formula 3 are subjected to the ether-forming reaction as shown below to obtain the compound represented by formula 1,

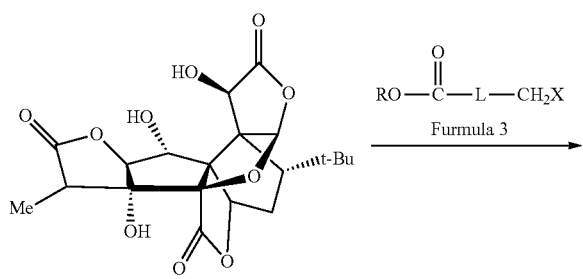

Furmula 3

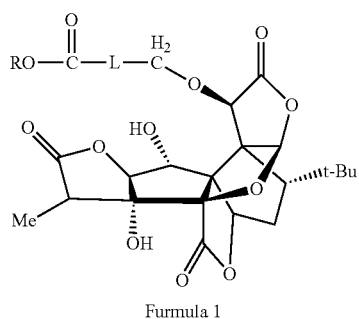

Furmula 1 wherein, R and L are as defined above, and X is halogen.

In the ether-forming reaction, the X is preferably fluorine, chlorine, bromine or iodine, further preferably chlorine, bromine or iodine.

In the ether-forming reaction, the organic solvent may be an organic solvent conventional in the art for this type of reaction, the organic solvent in the present disclosure is particularly preferably one or more of halogenated hydrocarbon solvents, ether solvents, ketone solvents, nitrile solvents and amide solvents. The halogenated hydrocarbon solvent is preferably dichloromethane and/or chloroform. The ether solvent is preferably tetrahydrofuran and/or dioxane, and more preferably tetrahydrofuran. The ketone solvent is preferably acetone and/or butanone. The nitrile solvent is preferably acetonitrile. The amide solvent is preferably N,N-dimethylformamide.

In the ether-forming reaction, the base may be a base conventional in the art for this type of reaction, such as organic base and/or inorganic base. The organic base is preferably amine organic base, and more preferably one or more of triethylamine, pyrrolidine and piperazine. The inorganic base is preferably carbonate and/or bicarbonate. The carbonate is preferably one or more of sodium carbonate, potassium carbonate and cesium carbonate. The bicarbonate is preferably sodium bicarbonate.

In the ether-forming reaction, the catalyst may be a catalyst conventional in the art for this type of reaction, the catalyst in the present disclosure is particularly preferably iodide, further preferably one or more of potassium iodide, sodium iodide and cuprous iodide, and most preferably potassium iodide.

In the ether-forming reaction, the molar concentration of Ginkgolide B in the organic solvent may be a molar concentration conventional in the art for this type of reaction, the molar concentration in the present disclosure is particularly preferably 0.001 to 1 mol/L, further preferably 0.001 to 0.5 mol/L, further more preferably 0.001 to 0.1 mol/L (e.g., 0.025 mol/L, 0.024 mol/L, 0.023 mol/L).

In the ether-forming reaction, the molar ratio of Ginkgolide B to the compound represented by formula 3 may be a molar ratio conventional in the art for this type of reaction, the molar ratio in the present disclosure is particularly preferably 1:1 to 1:5, and further preferably 1:1 to 1:3 (e.g., 1:2).

In the ether-forming reaction, the molar ratio of Ginkgolide B to the base may be a molar ratio conventional in the art for this type of reaction, the molar ratio in the present disclosure is particularly preferably 1:1 to 1:10, and further preferably 1:3 to 1:6 (e.g., 1:4.6, 1:4.4).

In the ether-forming reaction, the molar ratio of Ginkgolide B to the catalyst may be a molar ratio conventional in the art for this type of reaction, the molar ratio in the present disclosure is particularly preferably 1:1 to 1:5, and further preferably 1:1 to 1:3 (e.g., 1:2).

In the ether-forming reaction, the reaction process may be monitored by conventional monitoring methods in the art (e.g., TLC, HPLC, or NMR), generally, when substantial disappearance of Ginkgolide B is monitored, the reaction reaches its endpoint. The reaction time of the present disclosure is particularly preferably 1 to 5 hours, further preferably 1 to 3 hours (e.g., 2 hours).

The reaction temperature of the ether-forming reaction may be the reaction temperature conventional in the art for this type of reaction, the reaction temperature in the present disclosure is particularly preferably the temperature at which the organic solvent used is refluxed at normal temperature and atmospheric pressure.

In a preferred embodiment of the present disclosure, the ether-forming reaction comprises the following steps: the Ginkgolide B is mixed with the organic solvent, the compound represented by formula 3, the catalyst and the base are sequentially added, and the reaction of the catalyst and the base is carried out.

In a preferred embodiment of the present disclosure, the ether-forming reaction may further comprise a post-treatment step after the reaction is completed. The post-treatment steps may be a post-treatment step conventional in the art for this type of reaction, preferably filtration, concentration and purification. The purification method may be a conventional purification method in the art (e.g., column chromatography).

The present disclosure also provides a method for preparing a compound represented by formula 2, comprising the following steps:

In an organic solvent, under the action of an acid or a base, the compound represented by formula 1 is subjected to hydrolysis reaction as shown below to obtain a compound represented by formula 1 in which R is hydrogen; all kinds of salts represented by formula 2 may be obtained by salt-forming reaction between the compound and various bases.

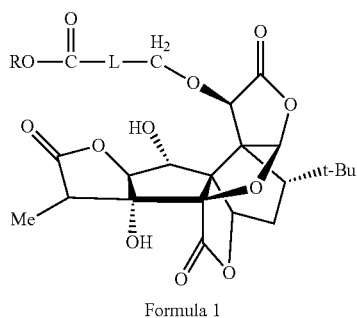 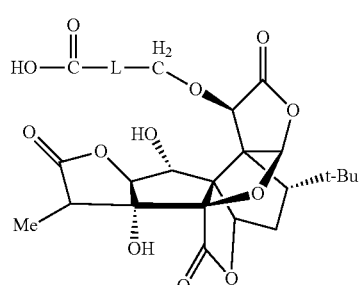

Formula 1          Hydrolysis          Formula 1 (R is hydrogen)

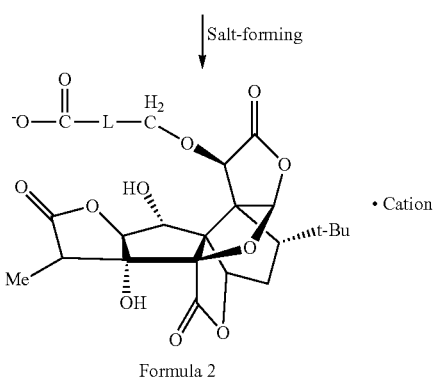

Formula 2 wherein, L and cation are as defined above;

R is substituted or unsubstituted $C_{1-8}$ hydrocarbonyl, and the "substituted or unsubstituted $C_{1-8}$ hydrocarbonyl" is as described above.

In the hydrolysis reaction, when the compound represented by formula 1 is subjected to the hydrolysis reaction under the action of the base, the organic solvent may be an organic solvent conventional in the art for this kind of reaction, the organic solvent of the present disclosure is particularly preferably alcohol solvent, and further preferably anhydrous alcohol solvent. The alcohol solvent is preferably one or more of methanol, ethanol, isopropanol and tert-butanol, and more preferably methanol. The organic solvent is preferably anhydrous methanol.

In the hydrolysis reaction, when the compound represented by formula 1 is subjected to the hydrolysis reaction under the action of the base, the base may be a base conventional in the art for this kind of reaction, such as inorganic base and/or organic base. The inorganic base is preferably one or more of hydroxide, carbonate and bicarbonate. The hydroxide is preferably one or more of lithium hydroxide, sodium hydroxide and potassium hydroxide. The carbonate is preferably one or more of sodium carbonate, potassium carbonate and cesium carbonate. The bicarbonate is preferably one or more of sodium bicarbonate, potassium bicarbonate and lithium bicarbonate. The organic base is preferably amine organic base and/or imine organic base, and more preferably one or more of triethylamine, pyridine, pyrrolidine and piperazine.

In the hydrolysis reaction, when the compound represented by formula 1 is subjected to the hydrolysis reaction under the action of the base, the molar ratio of the compound represented by formula 1 to the base may be a molar ratio conventional in the art for this type of reaction, the molar ratio in the present disclosure is particularly preferably 1:1 to 1:10, and further preferably 1:2 to 1:4 (e.g., 1:2.08, 1:2.78, 1:3.53).

In the hydrolysis reaction, when the compound represented by formula 1 is subjected to the hydrolysis reaction under the action of the base, the reaction temperature of the hydrolysis reaction may be the reaction temperature conventional in the art for this type of reaction, the reaction temperature in the present disclosure is particularly preferably the temperature at which the organic solvent used is refluxed at normal temperature and atmospheric pressure.

In the hydrolysis reaction, when the compound represented by formula 1 is subjected to the hydrolysis reaction under the action of the base, the reaction process may be monitored by conventional monitoring methods in the art (e.g., TLC, HPLC, or NMR), generally, when substantial disappearance of the compound represented by formula 1 is monitored, the reaction reaches its endpoint. The reaction time of the present disclosure is particularly preferably 1 to 5 hours, further preferably 3 to 4 hours (e.g., 3 hours).

In the hydrolysis reaction, when the compound represented by formula 1 is subjected to the hydrolysis reaction under the action of the base, the molar concentration of the compound represented by formula 1 in the organic solvent may be a molar concentration conventional in the art for this type of reaction, the molar concentration in the present disclosure is particularly preferably 0.001 to 1 mol/L, further preferably 0.001 to 0.5 mol/L, and further preferably 0.0034 to 0.16 mol/L (e.g., 0.034 mol/L, 0.06 mol/L, 0.16 mol/L).

In the hydrolysis reaction, when the compound represented by formula 1 is subjected to the hydrolysis reaction under the action of the acid, the organic solvent may be an organic solvent conventional in the art for this type of reaction, the organic solvent of the present disclosure is particularly preferably halogenated hydrocarbon solvent, further preferably one or more of dichloromethane, chloroform and carbon tetrachloride, and most preferably chloroform.

In the hydrolysis reaction, when the compound represented by formula 1 is subjected to the hydrolysis reaction under the action of the acid, the acid may be an acid conventional in the art for this kind of reaction, such as inorganic acid and/or organic acid. The inorganic acid is preferably one or more of hydrochloric acid, phosphoric acid, sulfuric acid and nitric acid. The organic acid is preferably one or more of trifluoroacetic acid, p-sulfonic acid and methanesulfonic acid.

In the hydrolysis reaction, when the compound represented by formula 1 is subjected to the hydrolysis reaction under the action of the acid, the molar ratio of the compound represented by formula 1 to the acid may be a molar ratio conventional in the art for this type of reaction, the molar ratio in the present disclosure is particularly preferably 1:2 to 1:100, and further preferably 1:50 to 1:70 (e.g., 1:61.5).

In the hydrolysis reaction, when the compound represented by formula 1 is subjected to the hydrolysis reaction under the action of the acid, the molar concentration of the compound represented by formula 1 in the organic solvent may be a molar concentration conventional in the art for this type of reaction, the molar concentration in the present disclosure is particularly preferably further preferably 0.001 to 1 mol/L, and further preferably 0.001 to 0.5 mol/L (e.g., 0.219 mol/L).

In the hydrolysis reaction, when the compound represented by formula 1 is subjected to the hydrolysis reaction under the action of the acid, the reaction temperature of the hydrolysis reaction may be the reaction temperature conventional in the art for this type of reaction, the reaction temperature in the present disclosure is particularly preferably 15 to 25° C.

In the hydrolysis reaction, when the compound represented by formula 1 is subjected to the hydrolysis reaction under the action of the acid, the reaction process may be monitored by conventional monitoring methods in the art (e.g., TLC, HPLC, or NMR), generally, when substantial disappearance of the compound represented by formula 1 is monitored, the reaction reaches its endpoint. The reaction time of the present disclosure is particularly preferably 1 to 5 hours, further preferably 1 to 4 hours (e.g., 2 hours).

In a preferred embodiment of the present disclosure, the hydrolysis reaction comprises the following steps: mixing the compound represented by formula 1 with the organic solvent, and adding the acid or base for reaction.

In a preferred embodiment of the present disclosure, the hydrolysis reaction may further comprise a post-treatment step after the reaction is completed, and the post-treatment step may be a post-treatment step conventional in the art. When the compound represented by formula 1 is subjected to the hydrolysis reaction under the action of the acid, the post-treatment step is preferably concentration. When the compound represented by formula 1 is subjected to the hydrolysis reaction under the action of the base, the post-treatment step is preferably pH adjustment of the reaction mixture to 3-4 at the end of the reaction, concentration and filtration. The reagent used for pH adjustment may be an acid conventional in the art, the reagent of the present disclosure is particularly preferably dilute hydrochloric acid.

The present disclosure also provides a preparation method of the compound represented by formula 2, comprising the following steps: in an organic solvent, the compound represented by formula 1 (R is hydrogen) is mixed with a base for salt-forming reaction.

In the salt-forming reaction, the organic solvent may be an organic solvent conventional in the art for this kind of reaction, the organic solvent of the present disclosure is particularly preferably alcohol solvent, and further preferably a mixed solvent of ethanol and methanol.

In the salt-forming reaction, the molar concentration of the compound represented by formula 1 (R is hydrogen) in the organic solvent may be a molar concentration conventional in the art for this kind of reaction, the molar concentration of the present disclosure is particularly preferably 0.01 to 0.1 mol/L, and further preferably 0.06 to 0.07 mol/L (e.g., 0.068 mol/L).

In the salt-forming reaction, the inorganic base is as described above.

In the salt-forming reaction, the organic base is as described above.

In the salt forming reaction, the molar ratio of the compound represented by formula 1(R is hydrogen) to the base may be a molar ratio conventional in the art for this kind of reaction, the molar ratio of the present disclosure is particularly preferably 1:1 to 3.

The reaction temperature of the salt-forming reaction may be a reaction temperature conventional in the art for this kind of reaction, the reaction temperature of the present disclosure is particularly preferably to be 15 to 40° C.

In the salt-forming reaction, the reaction process may be monitored by conventional monitoring methods in the art (e.g., TLC, HPLC, or NMR), generally, when substantial disappearance of the compound represented by formula 1 (R is hydrogen) is monitored, the reaction reaches its endpoint. The reaction time of the present disclosure is particularly preferably 1 to 4 hours, further preferably 1 to 2 hours (e.g., 1, 2 hours).

In a preferred embodiment of the present disclosure, the salt-forming reaction comprises the following steps: mixing the compound represented by formula 1 (R is hydrogen) with the organic solvent, adding the organic solvent dissolved with a base for reaction.

In a preferred embodiment of the present disclosure, the salt-forming reaction may further comprise a post-treatment step after the reaction is completed, and the post-treatment step may be a post-treatment step conventional in the art. In the present disclosure, the post-treatment step is particularly preferably recrystallization or direct concentration. The solvent used for recrystallization may be an organic solvent conventional in the art (e.g., diethyl ether).

The present disclosure also provides a pharmaceutical composition comprising a therapeutically effective dose of the compound represented by formula 1 or the pharmaceutically acceptable salt thereof as described above, or the pharmaceutically acceptable salt of the compound represented by formula 2 as described above.

The present disclosure also provides a use of the compound represented by formula 1 or the pharmaceutically acceptable salt thereof as described above, or the pharmaceutically acceptable salt of the compound represented by formula 2 as described above, or the pharmaceutical composition as described above in the preparation of medicaments for the prevention and treatment of diseases related to platelet activating factor such as ischemic stroke, thrombosis, angina pectoris, cardiopulmonary infarction, and inflammation or asthma.

The present disclosure also provides a method for the prevention and treatment of diseases related to platelet activating factor such as ischemic stroke, thrombosis, angina pectoris, cardiopulmonary infarction, and inflammation or asthma, comprising administering a therapeutically effective amount of the compound represented by formula 1 or the pharmaceutically acceptable salt of the compound represented by formula 2 or the pharmaceutical composition as described above to a subject.

The term "pharmaceutically acceptable salt" refers to the salt of the compound of the present disclosure, which is prepared from the compound with specific substituent discovered by the present disclosure and a relatively nontoxic base. The compounds of the present disclosure include relatively acidic functional groups, and base addition salts may be obtained by contacting the neutral form of such compounds with a sufficient amount of base in a pure solution or a suitable inert solvent. Pharmaceutically acceptable base addition salts include sodium, potassium, calcium, magnesium, zinc, ammonium, various organic ammonia, or various amino acid salts or similar salts.

The term "therapeutically effective dose" refers to a sufficient amount of a medication or medicament that is nontoxic but may achieve the desired effect. The determination of effective dose varies from person to person, and depends on the age and general condition of the subject, and also depends on the specific active substance, the appropriate effective dose in a case may be determined by the person skilled in the art according to routine tests.

The term "subject" refers to any animal that will or has received administration of the compound or the pharmaceutical composition according to the embodiment of the present disclosure, the subject is preferably mammals, more preferably humans. The term "mammal" includes any mammal. Examples of mammals include, but are not limited to, cattle, horses, sheep, pigs, cats, dogs, mice, rats, rabbits, guinea pigs, monkeys, humans, etc., and most preferably humans.

In the present disclosure, room temperature refers to 15 to 25° C. Normal temperature refers to 25° C. Atmospheric pressure refers to one atmosphere, 101 KPa. Overnight refers to 12 to 18 hours.

BRIEF DESCRIPTION OF THE DRAWINGS

Figure 4:
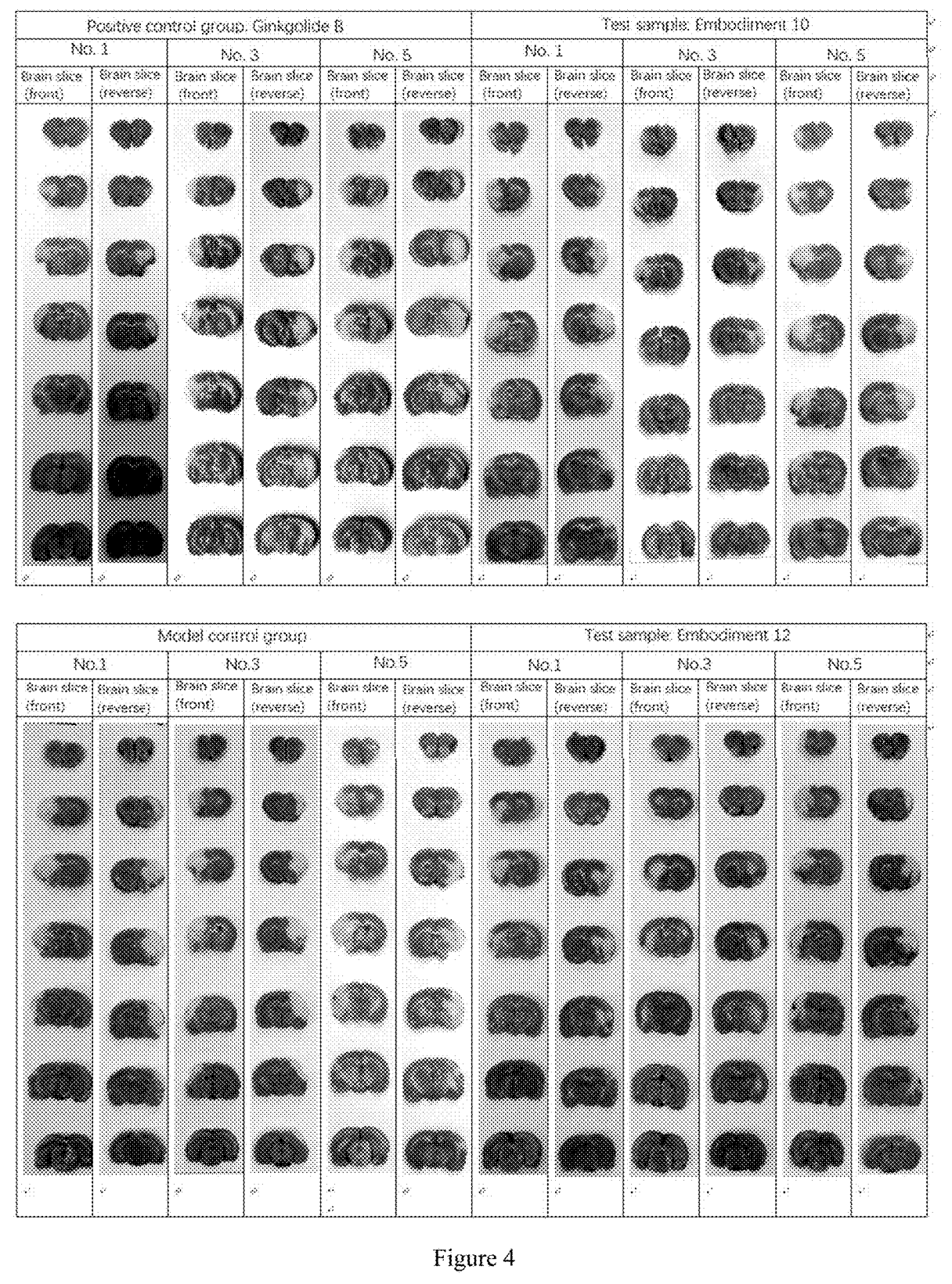

FIG. 4, partial slice photos of blank model group, Ginkgolide B, embodiment 10, and embodiment 12 group (original pictures are in color), Results: Embodiment 12 is significantly better than Ginkgolide B and embodiment 10, can significantly reduce the area ratio of hemicerebral infarction of acute cerebral ischemia in SD rats, and can be used for clinical anticoagulation and anti-cerebral ischemia, and the treatment of related diseases.

DETAILED DESCRIPTION OF THE EMBODIMENT

Figure 1:
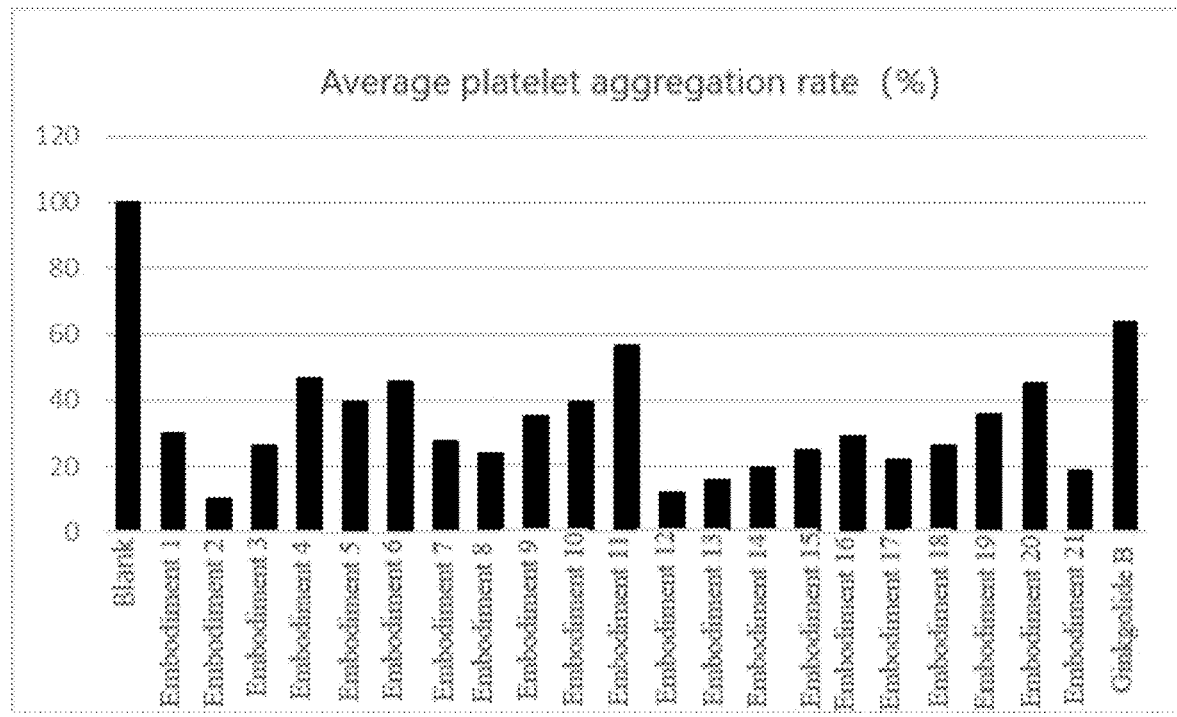
FIG. 1, test results of anti-platelet aggregation activity in vitro of embodiment 1-21 (n=5, 1 μM), Results: The compounds of the embodiments show obvious inhibitory effect on platelet aggregation, with blank as the standard 1, the platelet aggregation rate of Ginkgolide B at 1 μM concentration is 63.42%, and the platelet aggregation rate under the action of the compounds of each embodiment is lower than that of Ginkgolide B.

Embodiment 1 Preparation of 10-O-(methoxyformylmethyl) Ginkgolide B

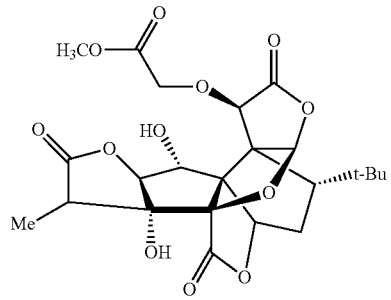

Chemical Formula: $C_{23}H_{28}O_{12}$
Exact Mass: 496.16 mg (0.5 mmol) of Ginkgolide B was dissolved in 20 mL of THF, 190 mg (2.0 mmol) of methyl chloroacetate, 166 mg (1.0 mmol) of KI and 310 mg (2.3 mmol) of potassium carbonate were added in turn, the mixture was heated, refluxed and stirred for 2 hours, and the plate layer was tracked until the substrate substantially disappeared, the post-treatment was carried out after the completion of the reaction, potassium carbonate was removed by filtration, the mother liquor was concentrated and the residue was separated by column chromatography to obtain a light yellow solid; then the residue was filtered and dried to obtain 121 mg of the product with a yield of 48%. $^1$H-NMR (DMSO-$d_6$, 400 MHz): 1.00 (s, 9H, t-Bu), 1.09 (d, 3H, 14-Me), 1.74 (dd, 1H, 8-H), 1.87 (ddd, 1H, 7α-H), 2.13 (dd, 1H, 7β-H), 2.79 (q, 1H, 14-H), 3.71 (s, 1H, —OCH$_3$), 4.06 (m, 1H, 1-H), 4.42 (d, 1H, J=16 Hz, 10-CH$_2$—), 4.63 (d, 1H, 2-H), 4.80 (d, 1H, J=16 Hz, 10-CH$_2$—), 5.15 (d, 1H, 1-OH), 5.29 (s, 1H, 10-H), 5.33 (d, 1H, 6-H), 6.19 (s, 1H, 12-H), 6.48 (s, 1H, 3-OH). MS (m/z): 497 (M+H$^+$)

Embodiment 2 Preparation of 10-O-(methoxyformylallyl) Ginkgolide B

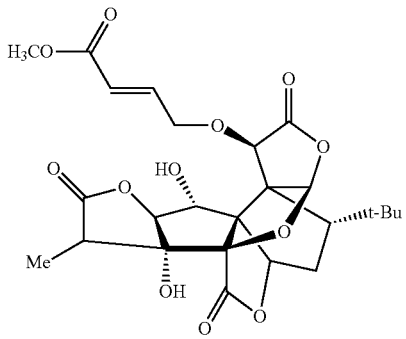

Chemical Formula: $C_{25}H_{30}O_{12}$
Exact Mass: 522.17

300 mg (0.71 mmol) of Ginkgolide B was dissolved in 30 mL of THF, 251 mg (1.4 mmol) of methyl 4-bromo-2-butenoate, 232 mg (1.4 mmol) of KI and 434 mg (3.1 mmol) of potassium carbonate were added in turn, the mixture was heated, refluxed and stirred for 2 hours, and the plate layer was tracked until the substrate substantially disappeared, the post-treatment was carried out after the completion of the reaction, potassium carbonate was removed by filtration, the mother liquor was concentrated and the residue was separated by column chromatography to obtain a light yellow solid, then the residue was filtered and dried to obtain 192 mg of the product with a yield of 52.5%. $^1$H-NMR (DMSO-$d_6$, 400 MHz): 1.01 (s, 9H, t-Bu), 1.08 (d, 3H, 14-Me), 1.74 (dd, 1H, 8-H), 1.87 (ddd, 1H, 7α-H), 2.13 (dd, 1H, 7β-H), 2.79 (q, 1H, 14-H), 3.73 (s, 1H, —OCH$_3$), 4.06 (m, 1H, 1-H), 4.42 (d, 1H, J=16 Hz, 10-CH$_2$—), 4.63 (d, 1H, 2-H), 4.80 (d, 1H, J=16 Hz, 10-CH$_2$—), 5.15 (d, 1H, 1-OH), 5.29 (s, 1H, 10-H), 5.33 (d, 1H, 6-H), 5.65 (m, 1H, —CH=), 5.76 (m, 1H, —CH=), 6.19 (s, 1H, 12-H), 6.48 (s, 1H, 3-OH). MS (m/z): 523 (M+H$^+$)

Embodiment 3 Preparation of 10-O-(tert-butoxyformylmethyl) Ginkgolide B

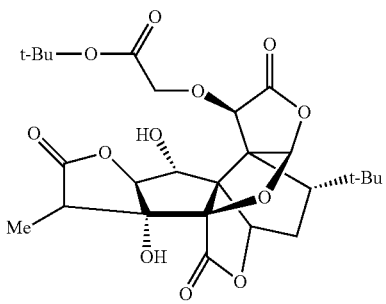

Chemical Formula: $C_{26}H_{34}O_{12}$
Exact Mass: 538.21

300 mg (0.70 mmol) of Ginkgolide B was dissolved in 30 mL of THF, 276 mg (1.41 mmol) of tert-butyl bromoacetate, 235 mg (1.41 mmol) of KI and 434 mg (3.2 mmol) of potassium carbonate were added in turn, the mixture was heated, refluxed and stirred for 2 hours, and the plate layer was tracked until the substrate substantially disappeared, the post-treatment was carried out after the completion of the reaction, potassium carbonate was removed by filtration, the mother liquor was concentrated and the residue was separated by column chromatography to obtain light yellow needle-like crystals; then the residue was filtered and dried to obtain 220 mg of the product with a yield of 58%. $^1$H-NMR (DMSO-$d_6$, 400 MHz): 0.99 (s, 9H, t-Bu), 1.09 (d, 3H, 14-Me), 1.42 (s, 9H, —O-t-Bu), 1.70 (dd, 1H, 8-H), 1.86 (ddd, 1H, 7α-H), 2.13 (dd, 1H, 7β-H), 2.79 (q, 1H, 14-H), 4.05 (m, 1H, 1-H), 4.28 (d, 1H, J=16 Hz, 10-CH$_2$—), 4.63 (d, 1H, 2-H), 4.65 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH). MS (m/z): 539 (M+H$^+$)

Embodiment 4 Preparation of 10-O-(methoxyformylmethoxyethyl) Ginkgolide B

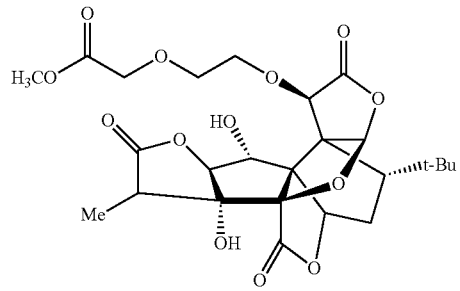

Chemical Formula: $C_{25}H_{32}O_{13}$
Exact Mass: 540.1843
Molecular Weight: 540.5138

300 mg (0.70 mmol) of Ginkgolide B was dissolved in 30 mL of THF, 345 mg (1.41 mmol) of methyl iodoethoxyacetate, 235 mg (1.41 mmol) of KI and 434 mg (3.2 mmol) of potassium carbonate were added in turn, the mixture was heated, refluxed and stirred for 2 hours, and the plate layer was tracked until the substrate substantially disappeared, the post-treatment was carried out after the completion of the reaction, potassium carbonate was removed by filtration, the mother liquor was concentrated and the residue was separated by column chromatography to obtain light yellow needle-like crystals; then the residue was filtered and dried to obtain 219 mg of the product with a yield of 58%. $^1$H-NMR (DMSO-$d_6$, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.57 (m, 4H, —OCH$_2$CH$_2$O—), 3.92 (s, 3H, —OCH$_3$), 4.05 (m, 1H, 1-H), 4.28 (d, 1H, J=16 Hz, 10-CH$_2$—), 4.63 (d, 11H, 2-H), 4.65 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH). MS (m/z): 541 (M+H$^+$)

Embodiment 5 Preparation of 10-O-(methoxyformylmethoxyethoxyethyl) Ginkgolide B

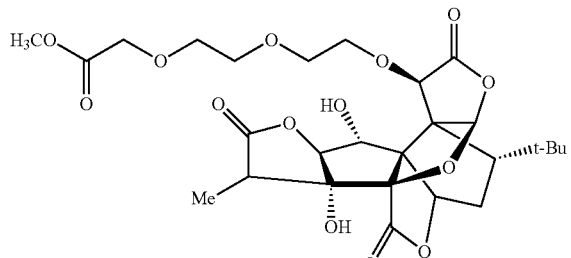

Chemical Formula: C₂₇H₃₆O₁₄
Exact Mass: 584.2105
Molecular Weight: 584.5663

300 mg (0.70 mmol) of GinkgolideB was dissolved in 30 mL of THF, 360 mg (1.49 mmol) of methyl bromoethoxyacetate, 235 mg (1.41 mmol) of KI and 434 mg (3.2 mmol) of potassium carbonate were added in turn, the mixture was heated, refluxed and stirred for 2 hours, and the plate layer was tracked until the substrate substantially disappeared, the post-treatment was carried out after the completion of the reaction, potassium carbonate was removed by filtration, the mother liquor was concentrated and the residue was separated by column chromatography to obtain light yellow needle-like crystals; then the residue was filtered and dried to obtain 231 mg of the product with a yield of 56%. ¹H-NMR (DMSO-d₆, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.52-3.59 (m, 8H, —OCH₂CH₂O—), 3.92 (s, 3H, —OCH₃), 4.05 (m, 1H, 1-H), 4.28 (d, 1H, J=16 Hz, 10-CH₂—), 4.63 (d, 1H, 2-H), 4.65 (d, 1H, J=16 Hz, 10-CH₂—), 5.13 (d, 1H, 1-OH), 5.25 (s, 1H, 10-H), 5.31 (d, 1H, 6-H), 6.19 (s, 1H, 12-H), 6.50 (s, 1H, 3-OH). MS (m/z): 585 (M–H⁺)

Embodiment 6 Preparation of 4-(Ginkgolide B-10-oxy)-2-butenoic Acid

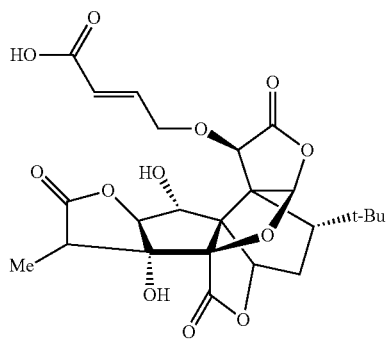

Chemical Formula: C₂₄H₂₈O₁₂
Exact Mass: 508.16

500 mg (0.96 mmol) of the product of embodiment 2 was dissolved in 6 mL of anhydrous methanol, 51 mg (2.0 mmol) of lithium hydroxide was added thereto, the mixture was heated, refluxed and stirred, the plate layer was tracked until the substrate substantially disappeared, the reaction was completed after 3 hours, the pH value was adjusted to about 4-5 with dilute hydrochloric acid, part of methanol was evaporated, the mixture was placed allowing solid to precipitate, then filtered to obtain 393 mg of the product with a yield of 80.6%. ¹H-NMR (DMSO-d₆, 400 MHz): 1.01 (s, 9H, t-Bu), 1.08 (d, 3H, 14-Me), 1.74 (dd, 1H, 8-H), 1.87 (ddd, 1H, 7α-H), 2.13 (dd, 1H, 7β-H), 2.79 (q, 1H, 14-H), 4.06 (m, 1H, 1-H), 4.42 (d, 1H, J=16 Hz, 10-CH₂—), 4.63 (d, 1H, 2-H), 4.80 (d, 1H, J=16 Hz, 10-CH₂—), 5.15 (d, 1H, 1-OH), 5.29 (s, 1H, 10-H), 5.33 (d, 1H, 6-H), 5.65 (m, 1H, —CH=), 5.76 (m, 1H, —CH=), 6.19 (s, 1H, 12-H), 6.48 (s, 1H, 3-OH), 13.67 (s, 1H, —COOH). MS (m/z): 507 (M–H⁺)

Embodiment 7 Preparation of 2-(Ginkgolide B-10-oxy)acetic Acid

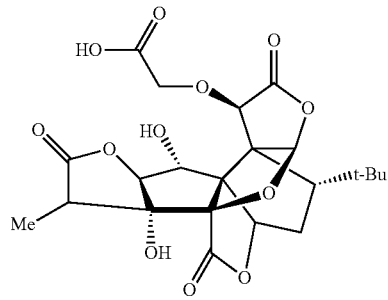

Chemical Formula: C₂₂H₂₆O₁₂
Exact Mass: 482.14

1.18 g (2.19 mmol) of the product of embodiment 3 was dissolved in 10 mL of chloroform, and 10 mL of trifluoroacetic acid was added, and stirred at room temperature, the plate layer was tracked until the substrate substantially disappeared. After 2 hours, the post-treatment of the reaction was finished, and the solvent was evaporated under reduced pressure to obtain a light yellow solid, then the residue was filtered and dried to obtain 1.05 g of the product with a yield of 99%. ¹H-NMR (DMSO-d₆, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH₂—), 4.62 (d, 1H, 2-H), 4.71 (d, 1H, J=16 Hz, 10-CH₂—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 13.70 (s, 1H, —COOH). MS (m/z): 481 (M–H⁺)

Embodiment 8 Preparation of 2-(Ginkgolide B-10-oxyethoxy)acetic Acid

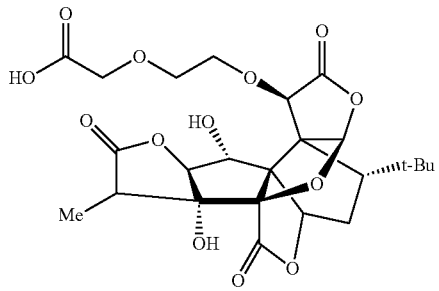

Chemical Formula: C₂₄H₃₀O₁₃
Exact Mass: 526.17

200 mg (0.37 mmol) of the product of embodiment 4 was dissolved in 6 mL of anhydrous methanol, 25 mg (1.0 mmol) of lithium hydroxide was added thereto. Then the mixture was heated, refluxed and stirred, the plate layer was tracked until the substrate substantially disappeared, the reaction was completed after 3-4 hours. The pH was adjusted to about 4-5 with dilute hydrochloric acid, part of methanol was evaporated, the mixture was placed allowing solid to precipitate, then filtered to obtain 174 mg of the product with a yield of 91.9%. $^1$H-NMR (DMSO-d$_6$, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.57 (m, 4H, —OCH$_2$CH$_2$O—), 4.05 (m, 1H, 1-H), 4.28 (d, 1H, J=16 Hz, 10-CH$_2$—), 4.63 (d, 1H, 2-H), 4.65 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH), 12.8 (s, 1H, —COOH). MS (m/z): 525 (M–H$^+$)

Embodiment 9 Preparation of 2-(Ginkgolide B-10-oxyethoxyethoxy)acetic Acid

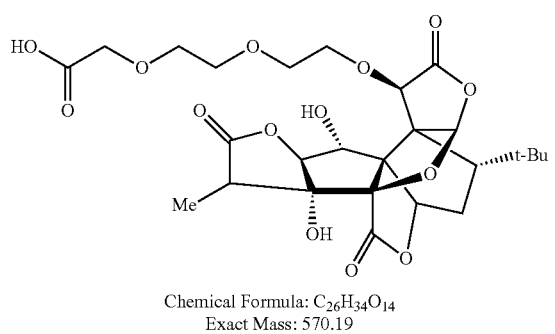

Chemical Formula: C$_{26}$H$_{34}$O$_{14}$
Exact Mass: 570.19

100 mg (0.17 mmol) of the product of embodiment 5 was dissolved in 5 mL of anhydrous methanol, 15 mg (0.6 mmol) of lithium hydroxide was added thereto, the mixture was heated, refluxed and stirred, the plate layer was tracked until the substrate substantially disappeared, the reaction was completed after 3-4 hours. The pH value was adjusted to about 4-5 with dilute hydrochloric acid, part of methanol was evaporated, the mixture was placed allowing solid to precipitate, then filtered to obtain 82 mg of the product with a yield of 84.6%. $^1$H-NMR (DMSO-d$_6$, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.54-3.64 (m, 8H, —OCH$_2$CH$_2$O—), 4.05 (m, 1H, 1-H), 4.28 (d, 1H, J=16 Hz, 10-CH$_2$—), 4.63 (d, 1H, 2-H), 4.65 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH), 13.5 (s, 1H, —COOH). MS (m/z): 569 (M–H$^+$)

Embodiment 10 Preparation of 2-(Ginkgolide B-10-oxy)sodium Acetate

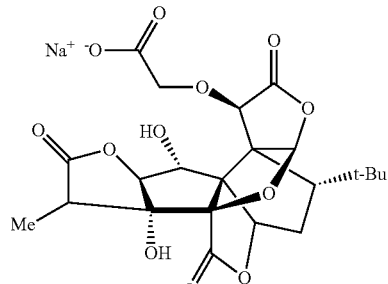

Chemical Formula: C$_{22}$H$_{25}$NaO$_{12}$
Exact Mass: 504.12

200 mg (0.41 mmol) of 2-(Ginkgolide B-10-oxy) acetic acid (embodiment 7) was dissolved in 2 mL of absolute ethanol, 2 times the molar amount of Na$_2$CO$_3$ in methanol solution was added dropwise, the mixture was stirred at room temperature for 1 hour, an equal volume of absolute ether was added, the mixture was placed overnight allowing solid to precipitate to obtain 185 mg of the product, with a yield of 89.5%. $^1$H-NMR (DMSO-d$_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH). MS (m/z): 481 (M–H$^+$, neg.).

Embodiment 11 Preparation of 2-(Ginkgolide B-10-oxy)ammonium Acetate

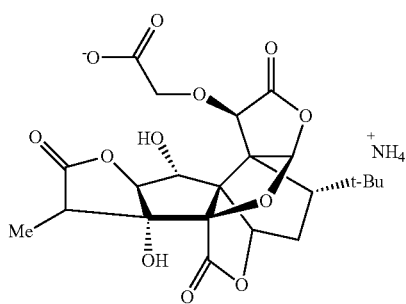

Chemical Formula: C$_{22}$H$_{29}$NO$_{12}$
Exact Mass: 499.1690
Molecular Weight: 499.4652

200 mg (0.41 mmol) of 2-(Ginkgolide B-10-oxy) acetic acid (embodiment 7) was dissolved in 2 mL of absolute ethanol, 2 times the molar amount of ammonia in methanol solution was added dropwise, and the mixture was stirred at room temperature for 2 hours, then the solvent was evaporated under reduced pressure, 10 mL of ether was added for washing, and then the mixture was filtered to obtain 197 mg of light yellow solid with a yield of 96.3%. $^1$H-NMR (DMSO-d$_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 8.10 (br-s, 4H, NH). MS (m/z): 481 (M–H$^+$, neg.).

Embodiment 12 Preparation of 2-(Ginkgolide B-10-oxy)lysine Acetate

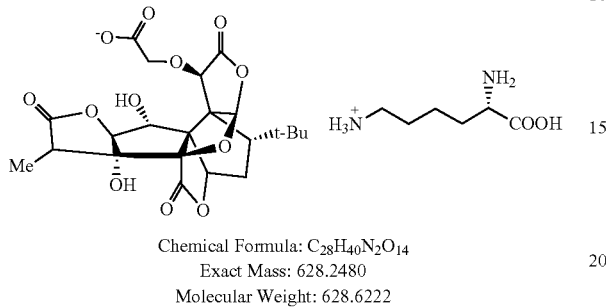

Chemical Formula: C$_{28}$H$_{40}$N$_2$O$_{14}$
Exact Mass: 628.2480
Molecular Weight: 628.6222

200 mg (0.41 mmol) of 2-(Ginkgolide B-10-oxy) acetic acid (embodiment 7) was dissolved in 2 mL of absolute ethanol, equal molar amount of lysine in methanol solution was added dropwise, and the mixture was stirred at room temperature for 2 hours, then the solvent was evaporated under reduced pressure, 10 mL of ether was added for washing, and then the mixture was filtered to obtain 255 mg of light yellow solid with a yield of 98.1%. $^1$H-NMR (DMSO-d$_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 1.25 (m, 2H, CH$_2$), 1.78 (m, 2H, CH$_2$), 2.03 (m, 2H, CH$_2$), 3.33 (m, 2H, CH$_2$), 3.48 (m, 1H, CH), 6.82 (br-s, 6H, NH). MS (m/z): 481 (M–H$^+$, neg.).

Embodiment 13 Preparation of 2-(Ginkgolide B-10-oxy)arginine Acetate

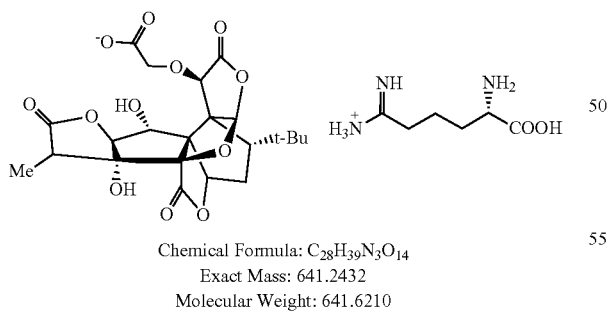

Chemical Formula: C$_{28}$H$_{39}$N$_3$O$_{14}$
Exact Mass: 641.2432
Molecular Weight: 641.6210

200 mg (0.41 mmol) of 2-(Ginkgolide B-10-oxy) acetic acid (embodiment 7) was dissolved in 2 mL of absolute ethanol, 1.5 times the molar amount of arginine in methanol solution was added dropwise, and the mixture was stirred at room temperature for 2 hours, then the solvent was evaporated under reduced pressure, 10 mL of ether was added for washing, and then the mixture was filtered to obtain 243 mg of light yellow solid with a yield of 92.5%. $^1$H-NMR (DMSO-d$_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 1.28 (m, 2H, CH$_2$), 1.35 (m, 2H, CH$_2$), 1.82 (m, 2H, CH$_2$), 3.49 (m, 1H, CH), 6.32-7.01 (br-s, 7H, N—H). MS (m/z): 481 (M–H$^+$, neg.).

Embodiment 14 Preparation of 2-(Ginkgolide B-10-oxy)histidine Acetate

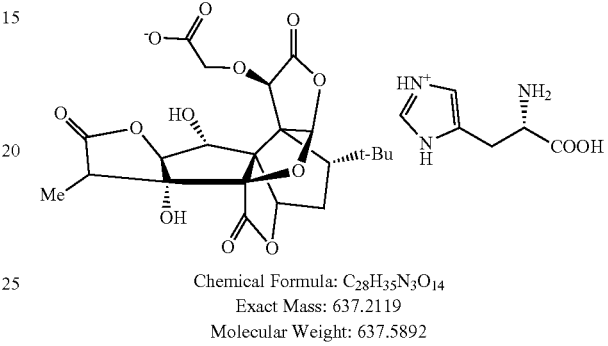

Chemical Formula: C$_{28}$H$_{35}$N$_3$O$_{14}$
Exact Mass: 637.2119
Molecular Weight: 637.5892

200 mg (0.41 mmol) of 2-(Ginkgolide B-10-oxy) acetic acid (embodiment 7) was dissolved in 2 mL of absolute ethanol, 1.8 times the molar amount of histidine in methanol solution was added dropwise, and the mixture was stirred at room temperature for 2 hours, then the solvent was evaporated under reduced pressure, 10 mL of ether was added for washing, and then the mixture was filtered to obtain 259 mg of light yellow solid with a yield of 99.1%. $^1$H-NMR (DMSO-d$_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 2.90-3.16 (m, 2H, CH$_2$), 4.49 (m, 1H, CH), 7.72 (s, 1H, CH), 8.91 (s, 1H, CH), 6.30-7.01 (br-s, 3H, N—H), 10.25 (br-s, 2H, N—H). MS (m/z): 481 (M–H$^+$, neg.).

Embodiment 15 Preparation of 2-(Ginkgolide B-10-oxy)triethylamine Acetate

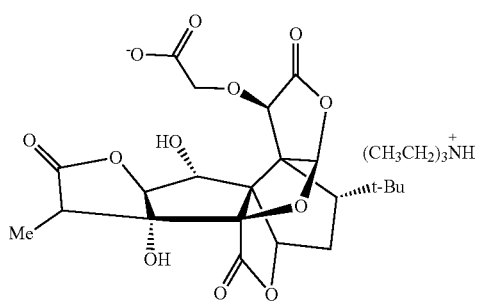

Chemical Formula: C$_{28}$H$_{41}$NO$_{12}$
Exact Mass: 583.2629
Molecular Weight: 583.6246

200 mg (0.41 mmol) of 2-(Ginkgolide B-10-oxy) acetic acid (embodiment 7) was dissolved in 2 mL of absolute ethanol, 2 times the molar amount of triethylamine in methanol solution was added dropwise, and the mixture was stirred at room temperature for 2 hours, then the solvent was evaporated under reduced pressure, 10 mL of ether was added for washing, and then the mixture was filtered to obtain 184 mg of light yellow solid with a yield of 76.9%. $^1$H-NMR (DMSO-$d_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 1.03 (t, 9H, CH$_3$—CH$_2$), 3.05 (q, 6H, CH$_3$—CH$_2$), 9.25 (br-s, 1H, N—H). MS (m/z): 481 (M–H$^+$, neg.).

Embodiment 16 Preparation of 2-(Ginkgolide B-10-oxy)diethylamine Acetate

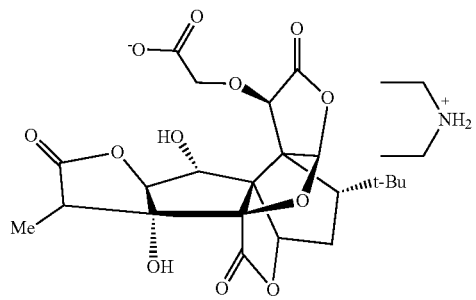

Chemical Formula: C$_{26}$H$_{37}$NO$_{12}$
Exact Mass: 555.2316
Molecular Weight: 555.5715

200 mg (0.41 mmol) of 2-(Ginkgolide B-10-oxy) acetic acid (embodiment 7) was dissolved in 2 mL of absolute ethanol, equal molar amount of diethylamine in methanol solution was added dropwise, and the mixture was stirred at room temperature for 2 hours, then the solvent was evaporated under reduced pressure, 10 mL of ether was added for washing, and then the mixture was filtered to obtain 178 mg of light yellow solid with a yield of 78.2%. $^1$H-NMR (DMSO-$d_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 1.05 (t, 6H, CH$_3$—CH$_2$), 3.07 (q, 4H, CH$_3$—CH$_2$), 8.27 (br-s, 2H, N—H). MS (m/z): 481 (M–H$^+$, neg.).

Embodiment 17 Preparation of 2-(Ginkgolide B-10-oxy) n-pentylamine Acetate

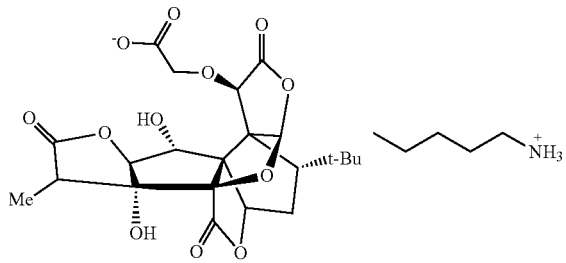

Chemical Formula: C$_{27}$H$_{39}$NO$_{12}$
Exact Mass: 569.2472
Molecular Weight: 569.5981

200 mg (0.41 mmol) of 2-(Ginkgolide B-10-oxy) acetic acid (embodiment 7) was dissolved in 2 mL of absolute ethanol, 3 times the molar amount of n-pentylamine in methanol solution was added dropwise, and the mixture was stirred at room temperature for 2 hours, then the solvent was evaporated under reduced pressure, 10 mL of ether was added for washing, and then the mixture was filtered to obtain 193 mg of light yellow solid with a yield of 82.7%. $^1$H-NMR (DMSO-$d_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 1.05 (m, 3H, CH$_3$—CH$_2$), 1.25-1.30 (m, 4H, —CH$_2$—CH$_2$), 2.05 (m, 2H, —CH$_2$), 3.37 (m, 2H, —CH$_2$), 7.27-7.55 (br-s, 3H, N—H). MS (m/z): 481 (M–H$^+$, neg.).

Embodiment 18 Preparation of 2-(Ginkgolide B-10-oxy) pyrrolidine Acetate

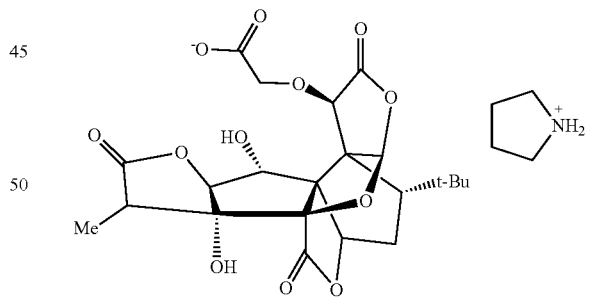

Chemical Formula: C$_{26}$H$_{35}$NO$_{12}$
Exact Mass: 553.2159
Molecular Weight: 553.5556

200 mg (0.41 mmol) of 2-(Ginkgolide B-10-oxy) acetic acid (embodiment 7) was dissolved in 2 mL of absolute ethanol, 1.5 times the molar amount of pyrrolidine in methanol solution was added dropwise, and the mixture was stirred at room temperature for 2 hours, then the solvent was evaporated under reduced pressure, 10 mL of ether was added for washing, and then the mixture was filtered to obtain 183 mg of light yellow solid with a yield of 80.7%.

$^1$H-NMR (DMSO-$d_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 2.02 (m, 4H, —CH$_2$), 3.17 (m, 4H, —CH$_2$), 7.27-7.55 (br-s, 2H, N—H). MS (m/z): 481 (M–H$^+$, neg.).

Embodiment 19 Preparation of 2-(Ginkgolide B-10-oxy)morpholine Acetate

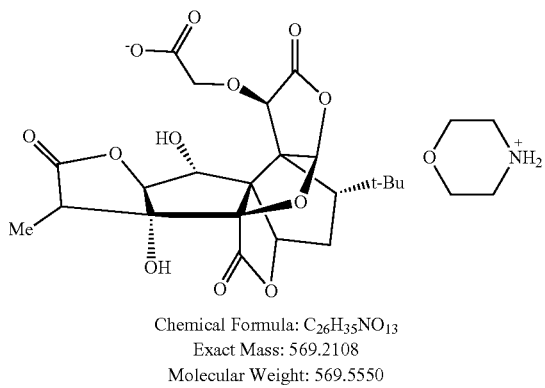

Chemical Formula: $C_{26}H_{35}NO_{13}$
Exact Mass: 569.2108
Molecular Weight: 569.5550

200 mg (0.41 mmol) of 2-(Ginkgolide B-10-oxy) acetic acid (embodiment 7) was dissolved in 2 mL of absolute ethanol, 1.5 times the molar amount of morpholine in methanol solution was added dropwise, and the mixture was stirred at room temperature for 2 hours, then the solvent was evaporated under reduced pressure, 10 mL of ether was added for washing, and then the mixture was filtered to obtain 202 mg of light yellow solid with a yield of 86.6%. $^1$H-NMR (DMSO-$d_6$, 400 MHz): 1.00 (s, 9H, t-Bu), 1.09 (d, 3H, 14-Me), 1.70 (dd, 1H, 8-H), 1.82 (ddd, 1H, 7α-H), 2.13 (dd, 1H, 7β-H), 2.80 (q, 1H, 14-H), 4.05 (d, 1H, 1-H), 4.29 (d, 1H, J=16 Hz, 10-CH$_2$—), 4.62 (d, 1H, 2-H), 4.75 (d, 1H, J=16 Hz, 10-CH$_2$—), 5.28 (s, 1H, 10-H), 5.32 (d, 1H, 6-H), 5.50 (s, 1H, 1-OH), 6.18 (s, 1H, 12-H), 6.48 (s, 1H, 3-OH), 3.52 (m, 4H, —CH$_2$), 4.20 (m, 4H, —CH$_2$), 7.28-7.35 (br-s, 2H, N—H). MS (m/z): 481 (M–H$^+$, neg.).

Embodiment 20 Preparation of 2-(Ginkgolide B-10-oxyethoxy)sodium Acetate

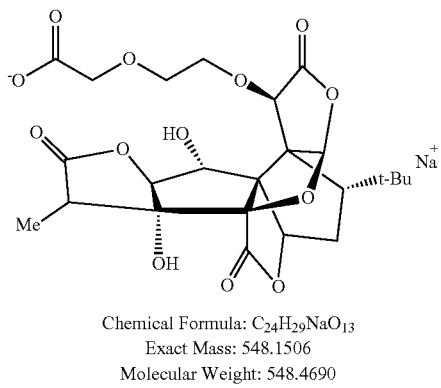

Chemical Formula: $C_{24}H_{29}NaO_{13}$
Exact Mass: 548.1506
Molecular Weight: 548.4690

250 mg (0.48 mmol) of 2-(Ginkgolide B-10-oxyethoxy) acetic acid (embodiment 8) was dissolved in 5 mL of absolute ethanol, 1.2 times the molar amount of sodium carbonate in methanol solution was added dropwise, and the mixture was stirred at room temperature for 2 hours, then the solvent was evaporated under reduced pressure, 10 mL of ether was added for washing, and then the mixture was filtered to obtain 208 mg of light yellow with a yield of 79.1%. $^1$H-NMR (DMSO-$d_6$, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.57 (m, 4H, —OCH$_2$CH$_2$O—), 4.05 (m, 1H, 1-H), 4.30 (d, 1H, J=16 Hz, 10-CH$_2$—), 4.63 (d, 1H, 2-H), 4.63 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH). MS (m/z): 525 (M–H$^+$, Neg.)

Embodiment 21 Preparation of 2-(Ginkgolide B-10-oxyethoxy)N-methyl-D-glucosamine Acetate

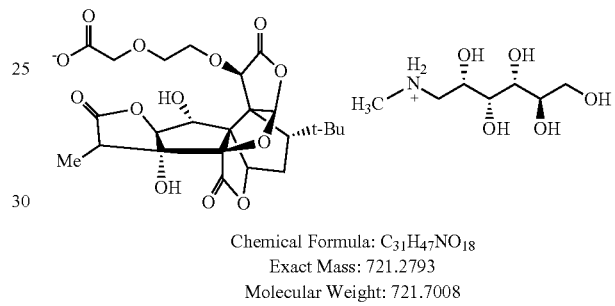

Chemical Formula: $C_{31}H_{47}NO_{18}$
Exact Mass: 721.2793
Molecular Weight: 721.7008 mg (0.48 mmol) of 2-(Ginkgolide B-10-oxyethoxy) acetic acid (embodiment 8) was dissolved in 5 mL of absolute ethanol, 1.5 times the molar amount of N-methyl-D-glucosamine in methanol solution was added dropwise, and the mixture was stirred at room temperature for 2 hours, then the solvent was evaporated under reduced pressure, 20 mL of ether was added for washing, and then the mixture was filtered to obtain 245 mg of light yellow solid with a yield of 70.8%. $^1$H-NMR (DMSO-$d_6$, 400 MHz): 0.98 (s, 9H, t-Bu), 1.09 (d, 3H, 14-Me), 1.70 (dd, 1H, 8-H), 1.86 (ddd, 1H, 7α-H), 2.13 (dd, 1H, 7β-H), 2.79 (q, 1H, 14-H), 3.57 (m, 4H, —OCH$_2$CH$_2$O—), 4.05 (m, 1H, 1-H), 4.28 (d, 1H, J=16 Hz, 10-CH$_2$—), 4.63 (d, 1H, 2-H), 4.65 (d, 1H, J=16 Hz, 10-CH$_2$—), 5.13 (d, 1H, 1-OH), 5.25 (s, 1H, 10-H), 5.31 (d, 1H, 6-H), 6.19 (s, 1H, 12-H), 6.50 (s, 1H, 3-OH), 2.85 (s, 3H, CH$_3$), 3.35-3.39 (m, 9H, CH, OH), 3.58-3.62 (m, 4H, CH$_{2*2}$), 8.89 (br-s, 2H, NH). MS (m/z): 525 (M–H$^+$)

Embodiment 22 In Vitro Anti-Platelet Aggregation Activity Evaluation Experiment

Experimental method: New Zealand white rabbits were anesthetized with sodium pentobarbital (2%, 2 mL/kg), about 40 mL of blood was obtained by abdominal aortic puncture, and the supernatant was collected as platelet-rich serum (PRP) after centrifugation at 1000 rpm/min for 10 min, the remaining blood was centrifuged at 4000 rpm/min for 10 min, and the supernatant was collected as platelet-poor serum (PPP); blank control group: 100 μL PRP+100 μL normal saline; drug group: 100 μL PRP+100 μL 0.05% DMSO dissolved drug (Ginkgolide B was positive control group), and the final drug concentration was 1 μM. After incubation for 5 min, 2 μL PAF(10× final concentration was 145 nm) was added; the platelet aggregation rate was measured by a platelet aggregation instrument, and each sample was repeated for five groups, the obtained aggregation rates were divided by the average value of the blank control group to obtain corrected values for comparison.

The results showed that the compounds of each embodiment exhibited obvious inhibitory effect on platelet aggregation, with blank as the standard 1, the platelet aggregation rate of Ginkgolide B at 1 μM concentration was 63.42%, and the platelet aggregation rate of the compounds of each embodiment was lower than that of Ginkgolide B, the specific data are shown in Table 1 and FIG. 1. Embodiments 2, 7, 12, 13, 14, 17 and 21 are compounds with significant activity.

TABLE 1

Test results of anti-platelet aggregation activity in vitro of Embodiment 1-21

| Compound number | Platelet aggregation rate (%, 1 μM) |
|---|---|
| blank | 100 |
| Embodiment 1 | 29.98 |
| Embodiment 2 | 10.30 |
| Embodiment 3 | 26.10 |
| Embodiment 4 | 46.70 |
| Embodiment 5 | 39.34 |
| Embodiment 6 | 45.67 |
| Embodiment 7 | 17.66 |
| Embodiment 8 | 23.68 |
| Embodiment 9 | 34.99 |
| Embodiment 10 | 39.34 |
| Embodiment 11 | 56.53 |
| Embodiment 12 | 12.23 |
| Embodiment 13 | 15.66 |
| Embodiment 14 | 19.74 |
| Embodiment 15 | 24.65 |
| Embodiment 16 | 28.87 |
| Embodiment 17 | 21.90 |
| Embodiment 18 | 26.45 |
| Embodiment 19 | 35.77 |
| Embodiment 20 | 45.32 |
| Embodiment 21 | 18.64 |
| Ginkgolide B | 63.42 |

Embodiment 23 Evaluation Experiment of Anticoagulant Activity in SD Rats

Experimental method: Rats were randomly divided into 10 rats in each group, and each group was given the corresponding test drug (50 mg/kg) by gavage after weighing, once a day for 3 days. One hour after the last administration, the rats were anesthetized, 8 mL of blood was taken from femoral artery, and the whole blood was anticoagulated with 3.8% sodium citrate, the whole blood anticoagulated with sodium citrate (3.8% trisodium citrate:whole blood=1:9) was centrifuged for 10 min at 800 r/min, and the upper plasma obtained at this speed was platelet-rich plasma (PRP), after PRP was sucked out, the remaining blood was centrifuged at 3000 r/min for 10 min, the plasma obtained at this speed was platelet poor plasma (PPP).

150 μL of PRP in each group was sucked and added to the 96-well plate (adjusted to zero by PPP), and ADP inducer was added, the absorbance value A1 was measured at the wavelength of 650 nm in the microplate reader, which was the absorbance value of each group at 0 min; the oscillation mode of the microplate reader was turned on, and the absorbance value A2 was detected again after 5 min, which was the absorbance value of each group at 5 min. Since the addition of ADP would cause platelet aggregation and change the light permeability, the maximum platelet aggregation rate (PAGM) within 5 min was measured according to this principle.

Maximum platelet aggregation rate(PAGM)=($A1-A2$)/$A1$×100

Figure 2:
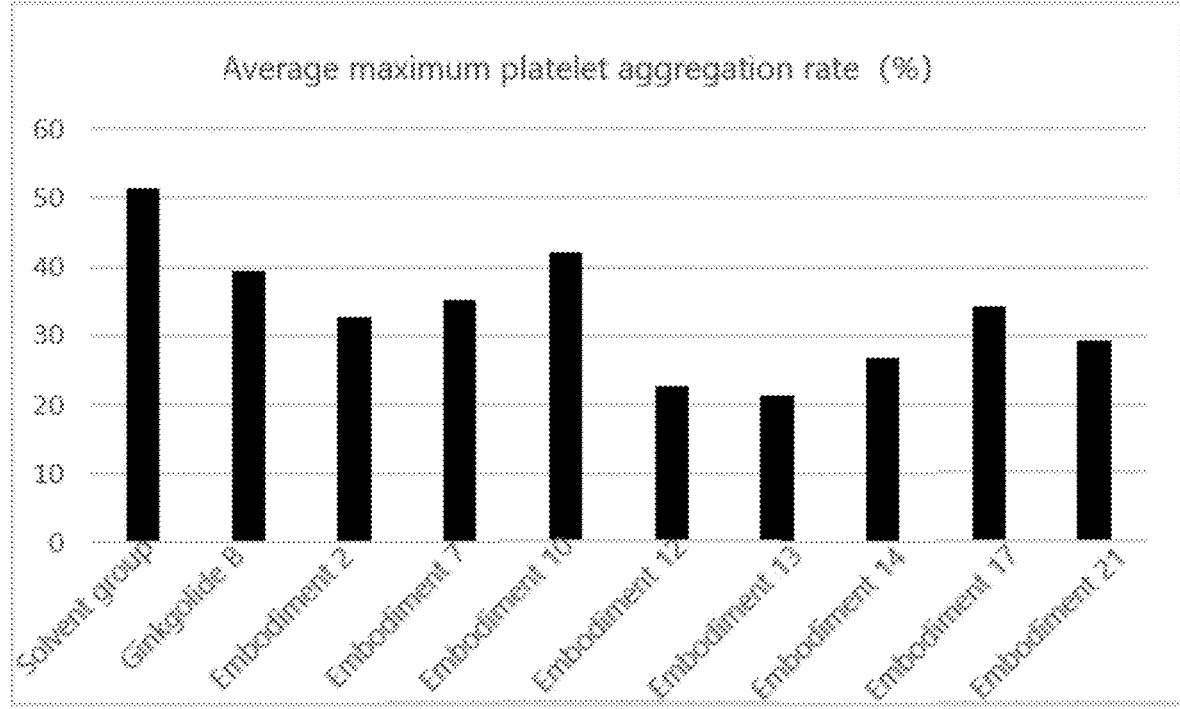
FIG. 2, evaluation results of embodiments 2, 7, 10, 12, 13, 14, 17 and 21 inhibiting platelet aggregation activity in SD rats (n=10, 50 mg/kg), Results: The embodiments show obvious anti-aggregation activity on platelet aggregation in SD rats, the activities of the compounds of the embodiments are higher than that of Ginkgolide B except for embodiment 10, and the in vivo activities of embodiments 12, 13 and 14 are particularly significant (P<0.001), which could be applied to clinical anticoagulation and treatment of related diseases.

The results are shown in table 2 and FIG. 2: all the embodiments exhibit obvious anti-aggregation activity on platelet aggregation in SD rats, the activities of the embodiments were higher than those of Ginkgolide B except for embodiment 10. The in vivo activities of embodiments 12, 13 and 14 were particularly significant, which could be applied to clinical anticoagulation and treatment of related diseases.

TABLE 2

Test results of anti-platelet aggregation activity in vitro of Embodiment 2, 7, 10, 12, 13, 14, 17 and 21 (n = 10).

| No. | Average maximum platelet aggregation rate (%) | Standard deviation (SD, %) |
|---|---|---|
| Solvent group | 51.45 | 12.10 |
| Ginkgolide B | 39.57 | 11.41 |
| Embodiment 2 | 32.60 | 9.50 |
| Embodiment 7 | 35.20 | 7.50 |
| Embodiment 10 | 42.20 | 9.52 |
| Embodiment 12 | 22.65 | 8.65 |
| Embodiment 13 | 21.25 | 7.65 |
| Embodiment 14 | 26.82 | 9.47 |
| Embodiment 17 | 34.20 | 8.60 |
| Embodiment 21 | 29.35 | 7.79 |

Embodiment 24 Evaluation Experiment of Anti-Acute Cerebral Ischemia Activity Methods: SD rats were weighed and randomly divided into 10 rats in each group, and were anesthetized by intraperitoneal injection of 15% chloral hydrate 300 mg/kg, their left lateral position was fixed on the rat operating table, and the left temporal top and face were shaved and disinfected with 75% ethanol, the skin was cut between the left eye and left ear, the temporal muscle and masseter muscle were passively separated, and the wing plate of the temporal bone was exposed, under the operating microscope, a 2 mm×2 mm bone window was ground with a cranial drill 1 mm from the union of the temporal bone and the temporal scalene near the mouth, and the skull was pried open with a pry bar. At this time, a relatively straight blood vessel with few branches can be seen through the dura mater, that is, the middle cerebral artery. Bipolar electrocoagulation forceps were used to cauterize the olfactory tract from 1 mm to the inferior cerebral vein, which completely blocked the blood flow. The temporal muscle and skin were sutured in turn, and then the rat was administered by gavage (50 mg/kg). After the rats were awakened, they were put back into their cages and continued to be reared for 24 h.

The rats were anesthetized by intraperitoneal injection of 15% chloral hydrate 300 mg/kg again, the brains were decapitated, the olfactory bulb, cerebellum and brain stem were removed, quick-frozen in the refrigerator at −20° C. for about 15 min, and then the frozen brains were cut into 7 slices. The brain slices were stained in 1% TTC dye solution (incubated at 37° C. in the dark for about 5-10 min), the infarcted area of brain slices after staining was white, while the non-infarcted area was rose red; after staining was completed, the brain slices were moved to 10% formaldehyde solution and kept away from light for 24 hours, finally, a digital camera was used to take pictures, the areas of frontal and reverse infarcted areas and non-infarcted areas were measured by image analysis software (ImageJ, version: 1.4.3.67), and the ratio of infarcted areas in the total infarcted cerebral hemisphere was calculated.

Figure 3:
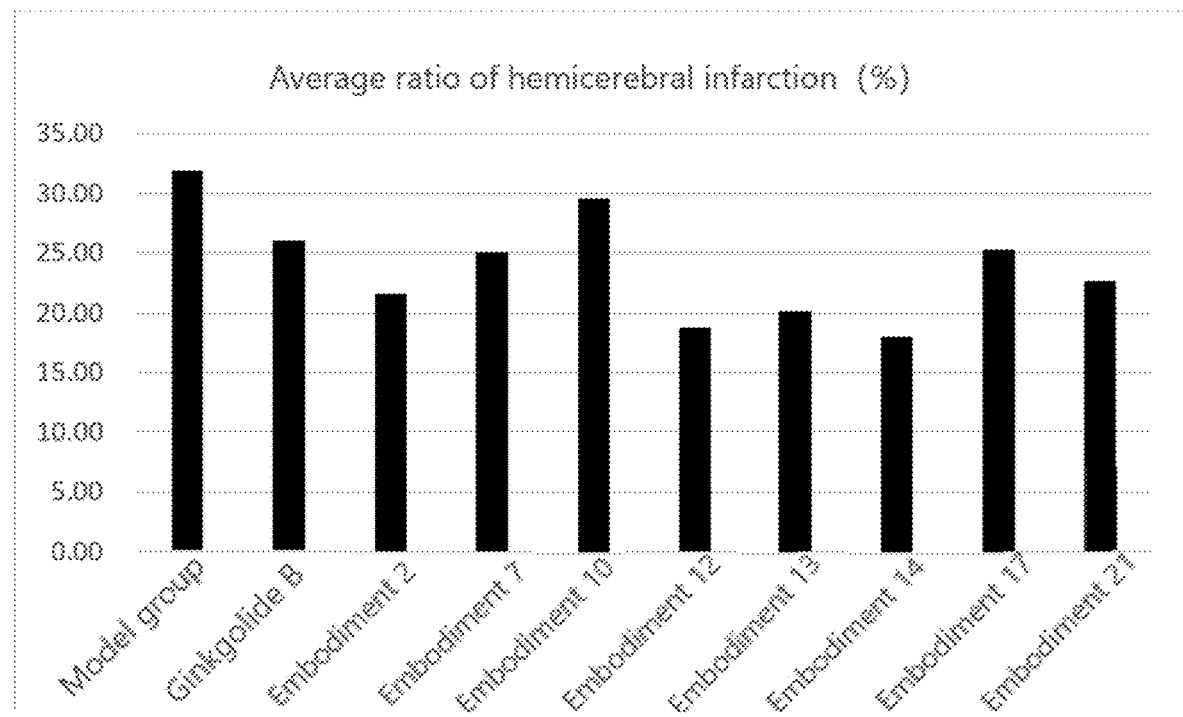
FIG. 3, evaluation results of the activity of embodiments 2, 7, 10, 12, 13, 14, 17 and 21 for reducing the area ratio of hemicerebral infarction in SD rats (n=10, 50 mg/kg), Results: Compared with the model group, the compounds of each embodiment can obviously reduce the area ratio of hemicerebral infarction in rats, the activities of the compounds in the embodiments are smaller than that of Ginkgolide B group except for embodiment 10, and the activities of embodiments 12, 13 and 14 are particularly significant (P<0.001), which can be used for clinical treatment of cerebral ischemia and cerebral ischemia related diseases.

The experimental results are shown in table 3 and FIG. 3: compared with the model group, the compounds of each embodiment can obviously reduce the ratio of hemispheric infarction area in rats. The hemispheric infarction area of each group was smaller than that of Ginkgolide B group except for embodiment 10, and the activities of embodiments 12, 13 and 14 were particularly significant, which can be used for clinical treatment of cerebral ischemia and cerebral ischemia related diseases.

FIG. 3. evaluation results of the activity of embodiments 2, 7, 10, 12, 13, 14 and 21 for reducing the hemicerebral infarction area ratio in SD rats(n=10)

| Compound | Average area ratio of hemicerebral infarction (%) | standard deviation |
|---|---|---|
| Model group | 31.91 | 1.66 |
| Ginkgolide B | 26.12 | 6.04 |
| Embodiment 2 | 21.56 | 4.35 |
| Embodiment 7 | 25.14 | 4.56 |
| Embodiment 10 | 29.61 | 3.00 |
| Embodiment 12 | 18.83 | 5.75 |
| Embodiment 13 | 20.14 | 5.27 |
| Embodiment 14 | 17.98 | 4.76 |
| Embodiment 17 | 25.31 | 5.13 |
| Embodiment 21 | 22.66 | 3.67 |

Although the specific embodiments of the present disclosure have been described above, those skilled in the art should understand that these are only examples, various changes or modifications can be made to these embodiments without departing from the principle and essence of the present invention. Therefore, the protection scope of the present disclosure is defined by the appended claims.

What is claimed is:

1. A compound represented by formula 2,

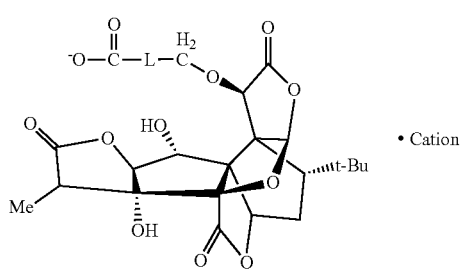

Formula 2

• Cation wherein:

L is —CH=CH—, —CH$_2$OCH$_2$—, —CH$_2$OCH$_2$CH$_2$OCH$_2$—, or L is absent;

and the cation in the compound is

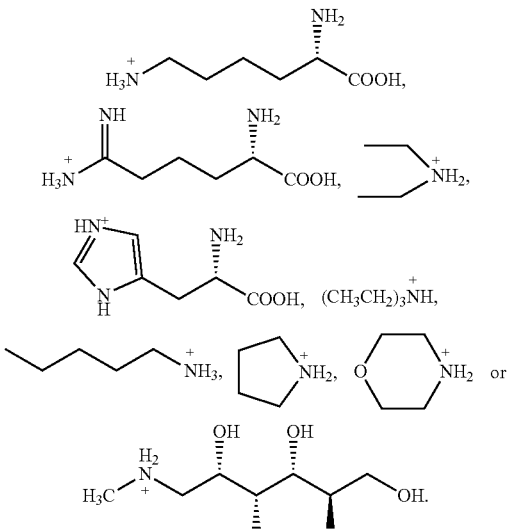

2. The compound represented by formula 2 according to claim 1, wherein, the compound represented by formula 2 is selected from the group consisting of:

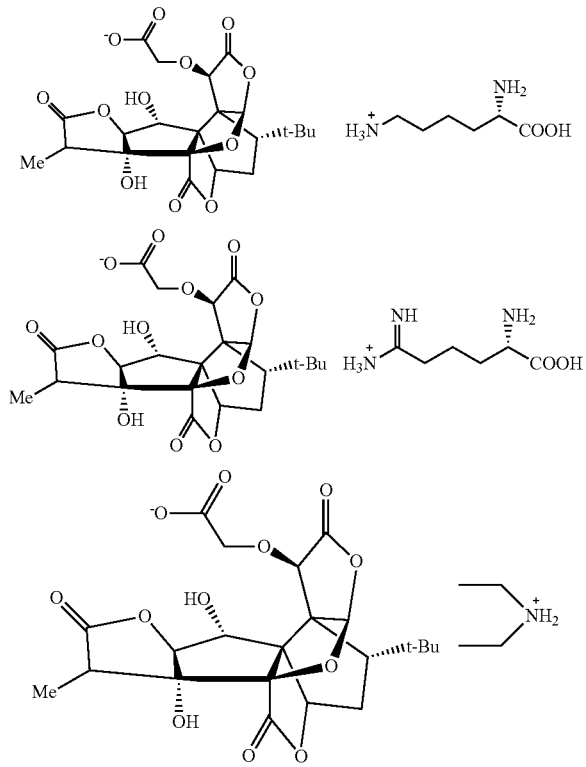

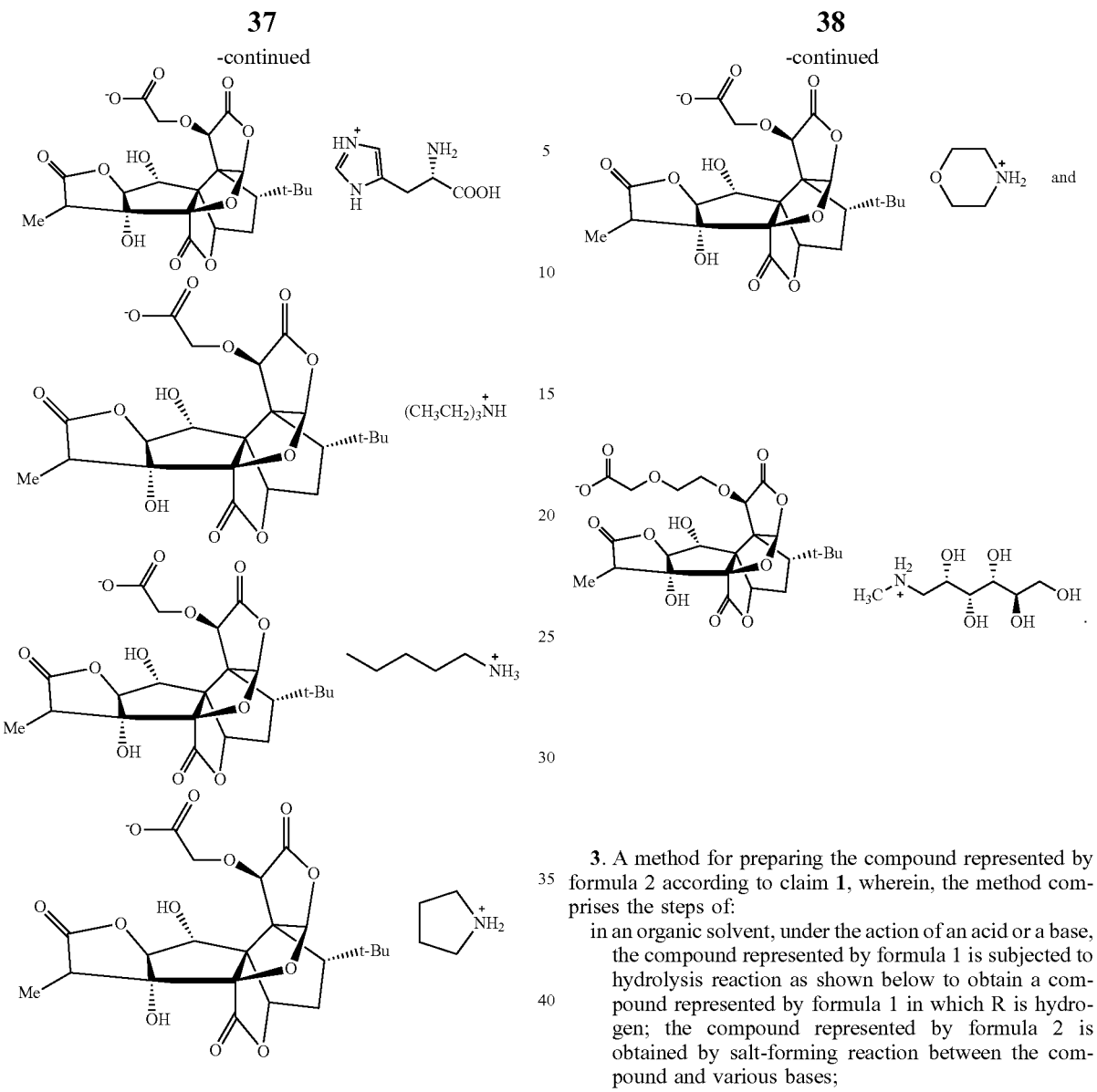

3. A method for preparing the compound represented by formula 2 according to claim 1, wherein, the method comprises the steps of:

in an organic solvent, under the action of an acid or a base, the compound represented by formula 1 is subjected to hydrolysis reaction as shown below to obtain a compound represented by formula 1 in which R is hydrogen; the compound represented by formula 2 is obtained by salt-forming reaction between the compound and various bases;

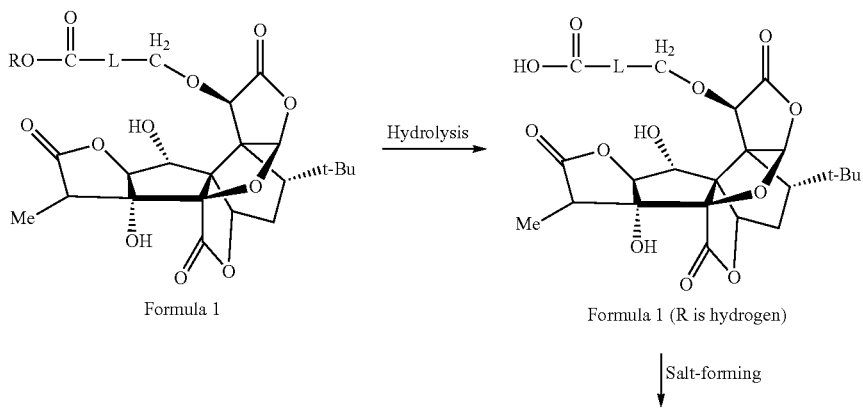

-continued

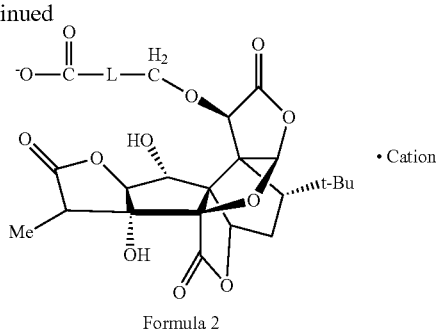

Formula 2 wherein:

L and cation are as defined in claim 1; and

R is substituted or unsubstituted $C_{1-8}$ hydrocarbonyl, the substituent in the substituted $C_{1-8}$ hydrocarbonyl is one or more of halogen, hydroxyl, $C_{1-10}$ alkoxy, phenyl and $C_{1-10}$ alkyl.

4. The method for preparing the compound represented by formula 2 according to claim 3, wherein for the hydrolysis reaction:

the base is inorganic base and/or organic base; or the acid is inorganic acid and/or organic acid; or the organic solvent is alcohol solvent and halogenated hydrocarbon solvent; or when the compound represented by formula 1 is subjected to the hydrolysis reaction under the action of the base, the molar ratio of the compound represented by formula 1 to the base is 1:1 to 1:10; or when the compound represented by formula 1 is subjected to the hydrolysis reaction under the action of the base, the reaction temperature of the hydrolysis reaction is the temperature at which the organic solvent used is refluxed at normal temperature and atmospheric pressure; or when the compound represented by formula 1 is subjected to the hydrolysis reaction under the action of the base, the reaction time is 1 to 5 hours; or when the compound represented by formula 1 is subjected to the hydrolysis reaction under the action of the base, the molar concentration of the compound represented by formula 1 in the organic solvent is 0.001 to 1 mol/L; or when the compound represented by formula 1 is subjected to the hydrolysis reaction under the action of the acid, the molar ratio of the compound represented by formula 1 to the acid is 1:2 to 1:100; or when the compound represented by formula 1 is subjected to the hydrolysis reaction under the action of the acid, the molar concentration of the compound represented by formula 1 in the organic solvent is 0.001 to 1 mol/L; or when the compound represented by formula 1 is subjected to the hydrolysis reaction under the action of the acid, the reaction temperature of the hydrolysis reaction is 15 to 25° C.; or when the compound represented by formula 1 is subjected to the hydrolysis reaction under the action of the acid, the reaction time is 1 to 5 hours.

5. D) The method for preparing the compound represented by formula 2 according to claim 3, wherein for the salt-forming reaction:

in an organic solvent, the compound represented by formula 1 (R is hydrogen) is mixed with a base for salt-forming reaction; or the organic solvent is alcohol solvent; or the molar concentration of the compound represented by formula 1 (R is hydrogen) in the organic solvent is 0.01 to 0.1 mol/L; or the molar ratio of the compound represented by formula 1 (R is hydrogen) to the base is 1:1 to 3; or the reaction temperature is 15 to 40° C.; or the reaction time is 1 to 4 hours.

6. A method for treating diseases related to platelet activating factor in a subject in need thereof, comprising:

administering an effective amount of the compound represented by formula 2 according to claim 1 to the subject, the disease related to platelet activating factor is ischemic stroke, thrombosis, angina pectoris, cardiopulmonary infarction, inflammation or asthma.

7. A pharmaceutical composition comprising a therapeutically effective dose of the compound represented by formula 2 according to claim 1.

8. The compound represented by formula 2 according to claim 1, wherein, the cation in the compound is

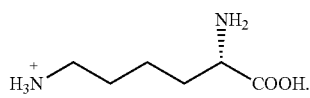

9. The compound represented by formula 2 according to claim 1, wherein, the cation in the compound is

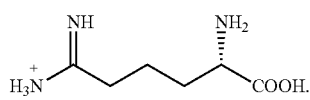

10. The compound represented by formula 2 according to claim 1, wherein, the cation in the compound is

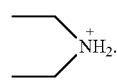

11. The compound represented by formula 2 according to claim 1, wherein, the cation in the compound is

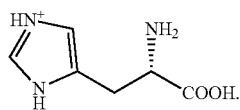

12. The compound represented by formula 2 according to claim 1, wherein, the cation in the compound is $(CH_3CH_2)_3{}^+NH$.

13. The compound represented by formula 2 according to claim 1, wherein, the cation in the compound is

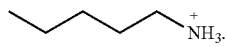

14. The compound represented by formula 2 according to claim 1, wherein, the cation in the compound is

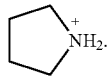

15. The compound represented by formula 2 according to claim 1, wherein, the cation in the compound is

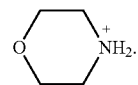

16. The compound represented by formula 2 according to claim 1, wherein, the cation in the compound is

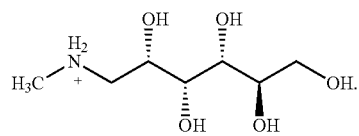

17. The compound represented by formula 2 according to claim 1, wherein, L is $-CH_2OCH_2-$, $-CH_2OCH_2CH_2OCH_2-$, or L is absent.

18. The compound represented by formula 2 according to claim 1, wherein, L is $-CH_2OCH_2-$, or L is absent.

19. The compound represented by formula 2 according to claim 1, wherein, L is $-CH_2OCH_2-$.

20. The compound represented by formula 2 according to claim 1, wherein, L is absent.

* * * * *